(12) United States Patent
Hiruma et al.

(10) Patent No.: US 9,464,133 B2
(45) Date of Patent: Oct. 11, 2016

(54) CDR-MODIFIED ANTI-SIGLEC-15 ANTIBODY

(71) Applicant: Daiichi Sankyo Company, Limited, Tokyo (JP)

(72) Inventors: Yoshiharu Hiruma, Tokyo (JP); Takako Kimura, Tokyo (JP); Hironari Shimizu, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 35 days.

(21) Appl. No.: 14/388,347

(22) PCT Filed: Mar. 29, 2013

(86) PCT No.: PCT/JP2013/059654
§ 371 (c)(1),
(2) Date: Sep. 26, 2014

(87) PCT Pub. No.: WO2013/147213
PCT Pub. Date: Oct. 3, 2013

(65) Prior Publication Data
US 2015/0056189 A1    Feb. 26, 2015

(30) Foreign Application Priority Data

Mar. 30, 2012  (JP) ................................. 2012-078842

(51) Int. Cl.
| | |
|---|---|
| A61K 39/00 | (2006.01) |
| A61K 39/395 | (2006.01) |
| C07K 16/00 | (2006.01) |
| C07K 16/18 | (2006.01) |
| C07K 16/22 | (2006.01) |
| C12N 5/10 | (2006.01) |
| C12N 15/13 | (2006.01) |
| C12N 15/63 | (2006.01) |
| C07K 16/28 | (2006.01) |
| A61K 45/06 | (2006.01) |
| C12P 21/02 | (2006.01) |

(52) U.S. Cl.
CPC ......... *C07K 16/18* (2013.01); *A61K 39/39533* (2013.01); *A61K 45/06* (2013.01); *C07K 16/2803* (2013.01); *C12P 21/02* (2013.01); *A61K 2039/505* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,855,808 B2 | 2/2005 | Goto et al. | |
| 7,125,686 B1 | 10/2006 | Goto et al. | |
| 7,205,397 B2 | 4/2007 | Goto et al. | |
| 7,276,344 B2 | 10/2007 | Goto et al. | |
| 7,405,037 B2 | 7/2008 | Greenwalt | |
| 7,468,268 B2 | 12/2008 | Goto et al. | |
| 7,608,704 B2 | 10/2009 | Yue et al. | |
| 7,989,160 B2 | 8/2011 | Sooknanan et al. | |
| 8,540,988 B2 | 9/2013 | Sooknanan et al. | |
| 8,546,540 B2 | 10/2013 | Hiruma et al. | |
| 8,575,316 B2 | 11/2013 | Hiruma et al. | |
| 2004/0023313 A1 | 2/2004 | Boyle et al. | |
| 2004/0033535 A1 | 2/2004 | Boyle et al. | |
| 2004/0076992 A1 | 4/2004 | Nakamura et al. | |
| 2009/0298763 A1 | 12/2009 | Sooknanan et al. | |
| 2010/0104575 A1 | 4/2010 | Sooknanan et al. | |
| 2011/0268733 A1 | 11/2011 | Hiruma et al. | |
| 2011/0311526 A1 | 12/2011 | Sooknanan et al. | |
| 2012/0230988 A1 | 9/2012 | Hiruma et al. | |
| 2012/0251485 A1 | 10/2012 | Hiruma et al. | |
| 2013/0280276 A1 | 10/2013 | Watanabe et al. | |
| 2014/0065146 A1 | 3/2014 | Hiruma et al. | |

FOREIGN PATENT DOCUMENTS

| | | |
|---|---|---|
| CA | 2 225 366 C | 10/2006 |
| EP | 1 580 263 A1 | 9/2005 |
| EP | 1 715 038 | 10/2006 |
| JP | 2007-020403 | 2/2007 |
| RU | 2 228 335 C2 | 8/1999 |
| RU | 2 238 948 C2 | 3/2004 |
| RU | 2 238 949 C2 | 10/2004 |
| WO | WO 98/46644 A1 | 10/1998 |
| WO | WO 02/38602 | 5/2002 |
| WO | WO 02/064771 | 8/2002 |
| WO | WO 03/048305 | 6/2003 |
| WO | WO 2005/113794 A1 | 12/2005 |
| WO | WO 2007/093042 | 8/2007 |
| WO | WO 2009/048072 | 4/2009 |
| WO | WO 2010/117011 A1 | 10/2010 |
| WO | WO 2011/041894 A1 | 4/2011 |

OTHER PUBLICATIONS

Protest Under 37 CFR § 1.291 filed Nov. 18, 2015, against U.S. Appl. No. 14/826,515, 301 pages.
Petitioner's Reply to Corrected Patent Owner's Response filed Nov. 30, 2015, in IPR2015-00291, 47 pages.
Declaration of Dr. Paul R. Crocker dated Dec. 1, 2015, filed Dec. 2, 2015, in IPR2015-00291, 7 pages.
Corrected Patent Owner's Response, Redacted Public Version, filed Sep. 28, 2015, in IPR2015-00291, 109 pages.
Declaration of Brendan F. Boyce, MD, Ch.B.. dated Sep. 6, 2015, 71 pages, served on Petitioner in IPR2015-00291 on Sep. 14, 2015.
Declaration of Kathryn E. Stein, Ph.D., dated Sep. 13, 2015, 51 pages, served on Petitioner in IPR2015-00291 on Sep. 14, 2015.
Rudikoff et al., "Single amino acid substitution altering antigen-binding specificity," Proc. Natl. Acad. Sci. USA, Mar. 1982, 79:1979-1983.
U.S. Appl. No. 14/388,342, filed Mar. 29, 2013, Hiruma et al.

(Continued)

*Primary Examiner* — Elizabeth C Kemmerer
(74) *Attorney, Agent, or Firm* — Foley & Lardner LLP

(57) ABSTRACT

Provided is a pharmaceutical composition for the treatment and/or prophylaxis of abnormal bone metabolism targeting a protein encoded by a gene strongly expressed in osteoclasts. Specifically provided is a pharmaceutical composition containing an antibody which specifically recognizes human Siglec-15 and has an activity of inhibiting osteoclast formation, and the like.

28 Claims, 5 Drawing Sheets

(56) References Cited

OTHER PUBLICATIONS

Abaza et al., "Effects of amino acid substitutions outside an antigenic site on protein binding to monoclonal antibodies of predetermined specificity obtained by peptide immunization: demonstration with region 94-100 (antigenic site 3) of myoglobin," J. Protein Chem., Oct. 1992, 11(5):433-444.
Akatsu et al., "Osteoclastogenesis inhibitory factor suppresses osteoclast survival by interfering in the interaction of stromal cells with osteoclast," Biochemical and Biophysical Research Communications, Sep. 18, 1998, 250(2):229-234.
Angata et al., "Siglec-15: an immune system Siglec c observed throughout vertebrate evolulation," Glycobiology, Aug. 2007, 17(8):838-846.
Bird et al., "Single-chain antigen-binding proteins," Science, 1988, 242(4877):423-426.
Buckley et al., "Human Osteoclast Culture From Peripheral Blood Monocytes," Methods in Molecular Medicine, 107:55-68, Human Cell Culture Protocols, Second Edition, 2005.
Casset et al., "A peptide mimetic of an anti-CD4 monoclonal antibody by rational design," Biochemical and Biophysical Research Communications, 2003, 307:198-205.
Chen et al., "Selection and Analysis of an Optimized Anti-VEGF Antibody: Crystal Structure of an Affinity-matured Fab in Complex with Antigen," J. Mol. Biol., 1999, 293:865-881.
Clackson et al., "Making antibody fragments using phage display libraries," 1991, Nature 352:624-628.
Collin-Osdoby et al., "RANKL-Mediated Osteoclast Formation from Murine RAW 264.7 Cells," Methods in Molecular Medicine, 80:153-166, Bone Research Protocols, 2003.
Colman, P.M., "Effects of amino acid sequence changes on antibody-antigen interactions," Res. Immunol., 1994, 145(1):33-36.
Daugherty et al., "Antibody affinity maturation using bacterial surface display," 1998, Protein Eng., 11:825-832.
Decision to Grant dated Aug. 13, 2014 in RU 2011128332, 24 pages, with English translation, 20 pages.
Decision to Grant issued in Russian Application No. 2010106639/10 on Sep. 17, 2012, with an English translation.
Duquesnoy, R.J., "Structural and functional definitions of epitopes reacting with mouse monoclonal antibodies," 2008, suppl. www/hlamatchmaker.net, 14 pages.
GenBank: BAA08453, human bone morphogenetic protein-3b (*Homo sapiens*), Dec. 27, 2006.
Harlow et al., Antibodies A Laboratory Manual, Cold Spring Harbor, New York, Cold Spring Harbor Laboratory Press, 1989, 141-155.
Hino et al., "cDNA Cloning and Genomic Structure of Human Bone Morphogenetic Protein-3b (BMP-3b)," Biochemical and Biophysical Research Communications, 1996, 223:304-310.
Hiruma et al., "Siglec-15, a member of the sialic acid-binding lectin is a novel regulator for osteoclast differentiation," Biochemical and Biophysical Research Communications, 2011, 409:424-429.
Holm et al., "Functional mapping and single chain construction of the anti-cytokeratin 8 monoclona antibody TS1," Molecular Immunology, 2007, 44:1075-1084.
Kania et al., "CD44 antibodies inhibit osteoclast formation," J. Bone Miner. Res., 1997, 12(8):1155-1164.
Kitaura et al., "An anti-c-Fms antibody inhibits orthodontic tooth movement," J. Dent. Res., 2008, 87(4):395-400.
Kussie et al., "A Single Engineered Amino Acid Substitution changes Antibody Fine Specificity," 1994, J. Immunology, 152(1):146-152.
Lederman et al., "A single amino acid substitution in a common African allele of the CD4 molecule ablates binding of the monoclonal antibody, OKT4," Mol. Immunol., 1991, 28(11):1171-1181.

Li et al., "Beta-Endorphin omission analogs: dissociation of immunoreactivity from other biological activities," PNAS USA, 1980, 77(6):3211-3214.
MacCallum et al., "Antibody-antigen Interactions: Contact Analysis and Binding Site Topography," J. Mol. Biol., 1996, 262:732-745.
Mirny et al., "Protein folding theory: From Lattice to All-Atom Models," Annu. Rev. Biophys. Biomol. Struct., 2001, 30:361-396.
Nakagawa et al., "RANK is the Essential Signaling Receptor for Osteoclast Differentiation Factor in Osteoclastogenesis," Biochemical and Biophysical Research Communications, 1998, 253:395-400.
Ngo et al., "Computational complexity, protein structure prediction, and the Levinthal paradox," The Protein Folding Problem, Birkhauser, 1994, Ch. 14:491-494.
Notice of Opposition to Grant of Patent dated Jun. 29, 2012, filed by Alethia Biotherapeutics Inc. against New Zealand Application 583397, 3 pages.
Owens et al., "The genetic engineering of monoclonal antibodies," J. Immunol. Methods, 1994, 168(2):149-165.
Paul et al., Fundamental Immunology, $3^{rd}$ Ed., 1993, 292-295.
Presta et al., "Antibody engineering for therapeutics," Current Opinion in Structural Biology, 2003, 13:519-525.
Protest to the Grant of a Patent dated Apr. 2, 2014, filed against Canadian Patent Application No. 2698326, 11 pages.
Russian Office Action dated Mar. 22, 2013 in Russian Appln. No. 2011128332/10(041966), English translation, 7 pages.
Siegel et al., "Antibody affinity optimization using yeast cell surface display," 2009, Methods Mol. Biol., 504:351-383.
Statement of Grounds and Particulars to Each Ground dated Jun. 1, 2012, filed by Alethia Biotherapeutics Inc. against Australian Patent Application 2008311698, 10 pages.
Takahashi et al., "A new treatment for osteoporosis using fully human monoclonal antibody to RANKL, AMG 162," Clin. Calcium, 2005, 15(1):43-48, with English summary on first page.
Teitelbaum, S.L., "Osteoclasts: What Do They Do and How Do They Do It?" 2007, AJP, 170(2):427-435.
Third Party Observations dated Aug. 13, 2012, filed by Alethia Biotherapeutics Inc. against European Patent Application 08838427.6, 5 pages.
Third Party Observations dated Aug. 20, 2012, filed by Alethia Biotherapeutics Inc. against European Patent Application 08838427.6, 4 pages.
Third Party Observations dated Dec. 10, 2012, filed by Alethia Biotherapeutics Inc. against European Patent Application 08838427.6, 7 pages.
Tsuda, Eisuke, "Hone Kyushi Yokuseiyaku Koho to shite no Hakotsu Saibo Keisei Yokusei Inshi OCIF/OPG, Ko-RANKL Kotai, Oyobi sono hoka no RANKL/RANK System Modulator," J. Jpn. Orthop. Assoc., 2005, 79(8):S753 (1-4-S6-3).
Tsuda, Eisuke, "Waga Kuni no Okeru Hone Ryoki no Soyaku no Rekishi Kaihatsu Chu no Hinmoke 6. Hakotsu Saibo Keisei Yokusei Inshi (OCIF/OPG), Ko RANKL Kotai, Oyobi Sono Ta no RANKL/RANK System Modulator," Bone, Jan. 2005, 19(1):85-92, Abstract only.
Vajdos et al., "Comprehensive Functional Maps of the Antigen-binding Site of an Anti-ErbB2 Antibody Obtained with Shotgun Scanning Mutanesis," J. Mol. Biol., 2002, 320:415-428.
Wada et al., "New bone density conservation agents for osteoporosis under research and development: Anti-RANKL antibody," Nihon Rinsho, 2007, 65(Suppl.9):459-462.
Woo et al., "Pharmacological Topics of Bone Metabolism: Antiresorptive Microbial Compounds That Inhibit Osteoclast Differentiation, Function, and Survival," J. Pharmacol. Sci., 2008, 106:547-554.
Saldanha, Jose W., "Molecular Engineering I: Humanization," Handbook of Therapeutic Antibodies, Chapter 6, Stephan Duebel, Ed., Jan. 1, 2007, 119-144, XP007913671.
Wu et al., "Simultaneous Humanization and Affinity Optimization of Monoclonal Antibodies," Methods in Molecular Biology, Jan. 1, 2003, 207:197-212.

Fig. 1

SEQ ID NO: 1: nucleotide sequence of K3-1115 antibody heavy chain (h#32A1-H1-1)
ATGAAACACCTGTGGTTCTTCCTCCTGCTGGTGGCAGCTCCCAGATGGGTGCTGAGCGAAGTCCAGCTTG
TGGAAAGCGGAGGGGGACTCGTTCAGCCAGGAGGCTCTCTGCGCCTGTCATGCGCTGCCAGCGGATTTAA
TTTCAATGATTATTTTATGAACTGGGTCAGGCAGGCTCCGGGAAAAGGGCTGGAATGGGTCGCCCAGATC
AGAAACAAGATCTATACTTACGCTACATTCTACGCCGCATCTGTAAAGGGGAGGTTTACAATTAGTCGCG
ACAATGCAAAAAATAGTCTGTATCTCCAAATGAACTCCCTCCGCGCAGAGGATACTGCTGTCTACTACTG
CGCCAGGTCCTTGACTGGCGGCGACTATTTTGATTACTGGGGACAGGGCACCCTGGTGACGGTGAGCTCA
GCCAGCACCAAGGGCCCTTCCGTGTTCCCTCTGGCCCCTTGTAGCCGTTCCACCAGCGAGTCCACCGCCG
CCCTTGGCTGTCTGGTGAAGGACTACTTCCCTGAGCCTGTGACCGTGAGCTGGAACTCCGGAGCCCTTAC
CAGCGGCGTGCACACCTTCCCTGCCGTGCTGCAGTCCAGCGGCCTTTACTCCCTGAGCTCCGTGGTGACC
GTGCCTAGCTCCAACTTCGGCACCCAAACCTACACCTGTAACGTGGACCACAAGCCTAGCAACACCAAGG
TGGACAAGACCGTGGAGCGTAAGTGTTGTGTGGAGTGTCCTCCTTGTCCTGCCCCTCCTGTGGCCGGACC
TTCCGTGTTCCTTTTCCCTCCTAAGCCTAAGGACACCCTGATGATCAGCCGTACCCCTGAGGTGACCTGT
GTGGTGGTGGACGTGTCCCACGAGGACCCTGAGGTGCAGTTCAACTGGTACGTGGACGGCGTGGAGGTGC
ACAACGCCAAGACCAAGCCTCGTGAGGAGCAATTCAACAGCACCTTCCGTGTGGTGTCCGTGCTTACCGT
GGTGCACCAAGACTGGCTGAACGGCAAGGAGTACAAGTGTAAGGTGAGCAACAAGGGACTTCCTGCCCCT
ATCGAGAAGACCATCTCCAAGACCAAGGGCCAACCTCGTGAGCCTCAAGTGTACACCCTTCCTCCTAGCC
GTGAGGAGATGACCAAGAACCAAGTGTCCCTTACCTGTCTGGTGAAGGGCTTCTACCCTAGCGACATCGC
CGTGGAGTGGGAGTCCAACGGACAACCTGAGAACAACTACAAGACCACCCCTCCTATGCTTGACAGCGAC
GGCTCCTTCTTCCTGTACAGCAAGCTGACCGTGGACAAGTCCCGTTGGCAACAAGGCAACGTGTTCAGCT
GTTCCGTGATGCACGAGGCCCTGCACAACCACTACACCCAAAAGAGCCTTTCCCTGAGCCCTGGAAAG
signal sequence (1-57), variable region (58-420), constant region (421-1398)

SEQ ID NO: 2: amino acid sequence of K3-1115 antibody heavy chain (h#32A1-H1-1)
MKHLWFFLLLVAAPRWVLSEVQLVESGGGLVQPGGSLRLSCAASGFNFNDYFMNWVRQAPGKGLEWVAQI
RNKIYTYATFYAASVKGRFTISRDNAKNSLYLQMNSLRAEDTAVYYCARSLTGGDYFDYWGQGTLVTVSS
ASTKGPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWLNGKEYKCKVSNKGLPAP
IEKTISKTKGQPREPQVYTLPPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
signal sequence (1-19), variable region (20-140), constant region (141-466)

Fig. 2

SEQ ID NO: 3: nucleotide sequence of K3-1115 antibody light chain (h#32A1-L2-15)

ATGGTGCTGCAGACCCAGGTGTTCATCTCCCTGCTGCTGTGGATCTCCGGCGCATATGGCGAAATTCTGA
TGACGCAGAGTCCTGCAACTCTTAGTCTGTCACCTGGCGAGAGAGCCACACTCAGCTGCCGAGCGTCCCA
GTCCGTGACCATTAGCGGCTATTCTTTTATTCATTGGTATCAGCAAAAGCCTGGACAGGCGCCAAGGCTG
CTCATTTACAGAGCAAGCAACCTTGCCTCTGGCATTCCAGCAAGATTCAGCGGGAGCGGATCAGGGACAG
ATTTCACCTTGACCATCTCCTCCCTGGAGCCGGAGGATTTCGCGTTGTATTATTGTCAGCAATCTAGGAA
GAGTCCATGGACATTTGGCCAGGGCACCAAAGTGGAGATCAAGCGTACGGTGGCCGCCCCCTCCGTGTTC
ATCTTCCCCCCCTCCGACGAGCAGCTGAAGTCCGGCACCGCCTCCGTGGTGTGCCTGCTGAATAACTTCT
ACCCCAGAGAGGCCAAGGTGCAGTGGAAGGTGGACAACGCCCTGCAGTCCGGGAACTCCCAGGAGAGCGT
GACCGAGCAGGACAGCAAGGACAGCACCTACAGCCTGAGCAGCACCCTGACCCTGAGCAAAGCCGACTAC
GAGAAGCACAAGGTGTACGCCTGCGAGGTGACCCACCAGGGCCTGAGCTCCCCCGTCACCAAGAGCTTCA
ACAGGGGGGAGTGT signal sequence (1-60), variable region (61-399), constant region (400-714)

SEQ ID NO: 4: amino acid sequence of K3-1115 antibody light chain (h#32A1-L2-15)

MVLQTQVFISLLLWISGAYGEILMTQSPATLSLSPGERATLSCRASQSVTISGYSFIHWYQQKPGQAPRL
LIYRASNLASGIPARFSGSGSGTDFTLTISSLEPEDFALYYCQQSRKSPWTFGQGTKVEIKRTVAAPSVF
IFPPSDEQLKSGTASVVCLLNNFYPREAKVQWKVDNALQSGNSQESVTEQDSKDSTYSLSSTLTLSKADY
EKHKVYACEVTHQGLSSPVTKSFNRGEC signal sequence (1-20), variable region (21-133), constant region (134-238)

Fig. 3

SEQ ID NO: 5: nucleotide sequence of K3-1115/T103E antibody heavy chain
atgaaacacctgtggttcttcctcctgctggtggcagctcccagatgggtgctgagcgaagtccagcttg
tggaaagcggaggggggactcgttcagccaggaggctctctgcgcctgtcatgcgctgccagcggatttaa
tttcaatgattatttatgaactgggtcaggcaggctccgggaaaagggctggaatgggtcgcccagatc
agaaacaagatctatacttacgctacattctacgccgcatctgtaaaggggaggtttacaattagtcgcg
acaatgcaaaaaatagtctgtatctccaaatgaactccctccgcgcagaggatactgctgtctactactg
cgccaggtccttggagggcggcgactattttgattactggggacagggcaccctggtgacggtgagctca
gccagcaccaagggcccttccgtgttccctctggccccttgtagccgttccaccagcgagtccaccgccg
cccttggctgtctggtgaaggactacttccctgagcctgtgaccgtgagctggaactccggagcccttac
cagcggcgtgcacaccttccctgccgtgctgcagtccagcggcctttactccctgagctccgtggtgacc
gtgcctagctccaacttcggcacccaaacctacacctgtaacgtggaccacaagcctagcaacaccaagg
tggacaagaccgtggagcgtaagtgttgtgtggagtgtcctccttgtcctgcccctcctgtggccggacc
ttccgtgttccttttccctcctaagcctaaggacaccctgatgatcagccgtacccctgaggtgacctgt
gtggtggtggacgtgtcccacgaggaccctgaggtgcagttcaactggtacgtggacggcgtggaggtgc
acaacgccaagaccaagcctcgtgaggagcaattcaacagccacttccgtgtggtgtccgtgcttaccgt
ggtgcaccaagactggctgaacggcaaggagtacaagtgtaaggtgagcaacaagggacttcctgcccct
atcgagaagaccatctccaagaccaagggccaacctcgtgagcctcaagtgtacacccttcctcctagcc
gtgaggagatgaccaagaaccaagtgtcccttacctgtctggtgaagggcttctaccctagcgacatcgc
cgtggagtgggagtccaacggacaacctgagaacaactacaagaccacccctcctatgcttgacagcgac
ggctccttcttcctgtacagcaagctgaccgtggacaagtcccgttggcaacaaggcaacgtgttcagct
gttccgtgatgcacgaggccctgcacaaccactacacccaaaagagcctttccctgagccctggaaag
signal sequence (1-57), variable region (58-420), constant region (421-1398)

SEQ ID NO: 6: amino acid sequence of K3-1115/T103E antibody heavy chain
MKHLWFFLLLVAAPRWVLSEVQLVESGGGLVQPGGSLRLSCAASGFNFNDYFMNWVRQAPGKGLEWVAQI
RNKIYTYATFYAASVKGRFTISRDNAKNSLYLQMNSLRAEDTAVYYCARSLEGGDYFDYWGQGTLVTVSS
ASTKGPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWLNGKEYKCKVSNKGLPAP
IEKTISKTKGQPREPQVYTLPPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
signal sequence (1-19), variable region (20-140), constant region (141-466)

Fig. 4

Amino acid sequences of respective CDRs of #32A1 antibody and K3-1115/T103E antibody SEQ ID NO: 7: CDRH1 of #32A1 antibody
(DYFMN)

SEQ ID NO: 8: CDRH2 of #32A1 antibody
(QIRNKIYTYATFYAESLEG)

SEQ ID NO: 9: CDRH2 of #32A1 antibody
(QIRNKIYTYATFYA)

SEQ ID NO: 10: CDRH3 of #32A1 antibody
(SLTGGDYFDY)

SEQ ID NO: 11: CDRH3 of K3-1115/T103E antibody
(SLEGGDYFDY)

SEQ ID NO: 12: CDRL1 of #32A1 antibody
(RASQSVTISGYSFIH)

SEQ ID NO: 13: CDRL2 of #32A1 antibody
(RASNLAS)

SEQ ID NO: 14: CDRL3 of #32A1 antibody
(QQSRKSPWT)

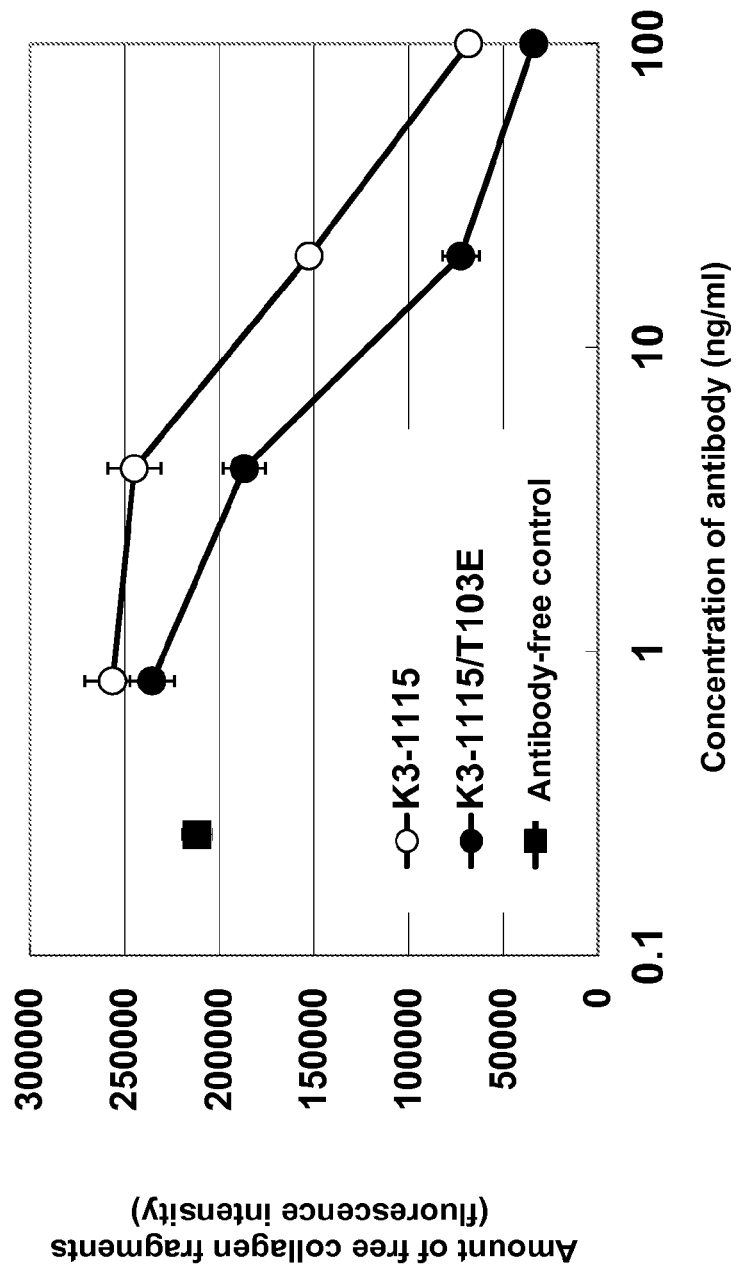
Fig. 5 Inhibition of bone resorption activity of normal osteoclast precursor cells by addition of K3-1115/T103E antibody

CDR-MODIFIED ANTI-SIGLEC-15 ANTIBODY

CROSS-REFERENCE TO RELATED APPLICATIONS

This application is a National Stage application of PCT/JP2013/059654, filed Mar. 29, 2013, which claims priority from Japanese application JP 2012-078842, filed Mar. 30, 2012.

TECHNICAL FIELD

The present invention relates to a substance useful as a therapeutic and/or prophylactic agent for abnormal bone metabolism, and a method for the treatment and/or prophylaxis of abnormal bone metabolism.

BACKGROUND ART

Bone is known to be a dynamic organ which is continuously remodeled by repeated formation and resorption so as to change its own morphology and maintain blood calcium levels. Healthy bone maintains an equilibrium between bone formation by osteoblasts and bone resorption by osteoclasts, and bone mass is maintained constant. In contrast, when the equilibrium between bone formation and bone resorption is lost, abnormal bone metabolism such as osteoporosis occurs (see, for example, Non Patent Literature 1 and 2).

As factors which regulate bone metabolism, many systemic hormones and local cytokines have been reported, and these factors collaborate with one another to form and maintain bone (see, for example, Non Patent Literature 1 and 3). As a change in bone tissue due to aging, the occurrence of osteoporosis is widely known, but the mechanism of its occurrence encompasses various factors such as a decrease in secretion of sex hormones and abnormality in the receptors for the hormones; variation in cytokine expression locally in bone; expression of aging genes; and osteoclast or osteoblast differentiation failure or dysfunction, and thus it is difficult to consider it as a simple age-related physiological phenomenon. Primary osteoporosis is largely divided into postmenopausal osteoporosis due to a decrease in secretion of estrogen and senile osteoporosis due to aging, but advancement of basic research on the mechanisms of regulation of bone formation and bone resorption is essential to elucidate the mechanism of its occurrence and to develop a therapeutic agent therefore.

Osteoclasts are multinucleated cells derived from hematopoietic stem cells, and by releasing chloride ions and hydrogen ions on a bone surface to which osteoclasts adhere, osteoclasts acidify the gap between the bone surface and the osteoclasts and also secrete cathepsin K which is an acid protease or the like (see, for example, Non Patent Literature 4). This causes degradation of calcium phosphate, activation of acid proteases and degradation of bone matrix proteins, resulting in bone resorption.

Osteoclast precursor cells have been found to be differentiated into osteoclasts by stimulation with RANKL (receptor activator of NF-κB ligand) expressed on the cell membrane of osteoblasts/stromal cells present on the surface of bone (see, for example, Non Patent Literature 5 and 6). It has been revealed that: RANKL is a membrane protein produced by osteoblasts/stromal cells, its expression is regulated by a bone resorption factor, RANKL induces differentiation of osteoclast precursor cells into mature multinucleated osteoclasts, and the like (see, for example, Non Patent Literature 5 and 7). Further, knockout mice devoid of RANKL have been found to develop an osteopetrosis-like disease, and therefore, RANKL has been proved to be a physiological osteoclast differentiation-inducing factor (see, for example, Non Patent Literature 8).

As medicaments for treating bone metabolism diseases or shortening the duration of treatment, bisphosphonates, active vitamin $D_3$, calcitonin and derivatives thereof, hormones such as estradiol, SERMs (selective estrogen receptor modulators), ipriflavone, vitamin $K_2$ (menatetrenone), PTH, calcium preparations, and the like are used. However, these medicaments are not always satisfactory in terms of therapeutic outcome and the development of a medicament with a more potent therapeutic effect has been demanded.

The cell membranes of immune cells are covered with a dense coating of various glycans such as sialylated glycans which are recognized by various glycan-binding proteins. Sialic-acid-binding immunoglobulin-like lectins (hereinafter referred to as "Siglecs") are a family of type I membrane proteins which recognize sialylated glycans and bind thereto. Many Siglecs are expressed on the cell membranes of immune cells and recognize sialic acid similarly present on the cell membranes of immune cells and regulate cell interaction or cell function and are considered to be involved in immune responses (see, for example, Non Patent Literature 9). However, there are also a lot of Siglec molecules whose physiological functions have not been elucidated yet. Siglec-15 (Sialic-acid binding immunoglobulin-like lectin 15) is a molecule which has been newly reported to belong to the Siglecs (see, for example, Non Patent Literature 10) and is identical to a molecule called CD33L3 (CD33 molecule-like 3). This molecule is highly evolutionarily conserved from fish to humans and has been found to be strongly expressed in dendritic cells and/or macrophages of human spleen and lymph nodes. Further, as a result of a binding test using a sialic acid probe, it has also been found that human Siglec-15 binds to Neu5Acα2-6GalNAc and that mouse Siglec-15 binds further to Neu5Acα2-3Galβ1-4Glc, and the like (see, for example, Non Patent Literature 10). Until recently, the physiological role of Siglec-15 had not been revealed, however, it has been reported that the expression of Siglec-15 increases with the differentiation and maturation of osteoclasts, and the differentiation of osteoclasts is inhibited by decreasing the expression of Siglec-15 by RNA interference (see, for example, PTL 1). Further, the effect of an anti-Siglec-15 antibody on osteoclast differentiation has been revealed for the first time in PTL 2 (published on Apr. 16, 2009) and PTL 3 (published on Oct. 14, 2010). Further, also in PTL 4, an antibody which inhibits the differentiation of osteoclasts has been disclosed, however, a search for an antibody which has a more potent effect has been continued.

PRIOR ART DOCUMENTS

Patent Literature

Patent Literature 1: WO 07/093042
Patent Literature 2: WO 09/48072
Patent Literature 3: WO 10/117011
Patent Literature 4: WO 11/041894

Non Patent Literature

Non Patent Literature 1: Endocrinological Review, (1992) 13, pp. 66-80

Non Patent Literature 2: Principles of Bone Biology, Academic Press, New York, (1996) pp. 87-102
Non Patent Literature 3: Endocrinological Review, (1996) 17, pp. 308-332
Non Patent Literature 4: American Journal of Physiology, (1991) 260, C1315-C1324
Non Patent Literature 5: Proceedings of the National Academy of Science of the United States of America, (1998) 95, pp. 3597-3602
Non Patent Literature 6: Cell, (1998) 93, pp. 165-176
Non Patent Literature 7: Journal of Bone and Mineral Research, (1998) 23, 5222
Non Patent Literature 8: Nature, (1999) 397, pp. 315-323
Non Patent Literature 9: Nature Reviews Immunology, (2007) 7, pp. 255-266
Non Patent Literature 10: Glycobiology, (2007) 17, pp. 838-846

SUMMARY OF INVENTION

Technical Problem of the Invention

An object of the invention is to provide a gene which is specifically expressed in various forms of abnormal bone metabolism which are seen in osteoporosis, rheumatoid arthritis, cancer metastasis to bone or the like, a substance which inhibits the differentiation and maturation of osteoclasts and the activity thereof, and a therapeutic and/or prophylactic agent for abnormal bone metabolism.

Means for Solving the Problem

The present inventors studied to elucidate the mechanism of osteoclast differentiation, maturation and activation in order to find a substance having a therapeutic and/or prophylactic effect on abnormal bone metabolism. As a result, the present inventors found that the expression of the Siglec-15 gene increases with the differentiation and maturation of osteoclasts, and also found that the differentiation of osteoclasts is inhibited by an antibody which specifically binds to Siglec-15. Further, the present inventors humanized a rat anti-mouse Siglec-15 antibody that had been obtained, and further modified the CDR of the humanized antibody, and thus completed the invention.

Specifically, the invention includes the following inventions.

(1) An antibody or an antigen binding fragment of the antibody, characterized in that:
the heavy chain sequence contains a variable region having CDRH1, CDRH2, and CDRH3, and the CDRH1 comprises an amino acid sequence represented by SEQ ID NO: 7, the CDRH2 comprises an amino acid sequence represented by SEQ ID NO: 9, and the CDRH3 comprises an amino acid sequence represented by SEQ ID NO: 11; and
the light chain sequence contains a variable region having CDRL1, CDRL2, and CDRL3, and the CDRL1 comprises an amino acid sequence represented by SEQ ID NO: 12, the CDRL2 comprises an amino acid sequence represented by SEQ ID NO: 13, and the CDRL3 comprises an amino acid sequence represented by SEQ ID NO: 14.

(2) The antibody or an antigen binding fragment of the antibody according to (1), characterized by comprising a heavy chain variable region sequence comprising amino acid residues 20 to 140 of an amino acid sequence represented by SEQ ID NO: 6 and a light chain variable region sequence comprising amino acid residues 21 to 133 of an amino acid sequence represented by SEQ ID NO: 4.

(3) The antibody or an antigen binding fragment of the antibody according to (1), characterized by comprising a heavy chain sequence comprising amino acid residues 20 to 466 of an amino acid sequence represented by SEQ ID NO: 6 and a light chain sequence comprising amino acid residues 21 to 238 of an amino acid sequence represented by SEQ ID NO: 4.

(4) The antibody or an antigen binding fragment of the antibody according to (1), characterized by comprising a heavy chain sequence comprising amino acid residues 20 to 465 of an amino acid sequence represented by SEQ ID NO: 6 and a light chain sequence comprising amino acid residues 21 to 238 of an amino acid sequence represented by SEQ ID NO: 4.

(5) The antigen binding fragment of the antibody according to (1) or (2), which is selected from the group consisting of Fab, F(ab')2, Fab' and Fv.

(6) The antibody according to (1) or (2), characterized by being an scFv.

(7) A pharmaceutical composition, characterized by comprising at least one of the antibodies or antigen binding fragments of the antibodies according to (1) to (6).

(8) The pharmaceutical composition according to (7), characterized by being a therapeutic and/or prophylactic agent for abnormal bone metabolism.

(9) A pharmaceutical composition for the treatment and/or prophylaxis of abnormal bone metabolism, characterized by comprising at least one of the antibodies or antigen binding fragments of the antibodies according to (1) to (6) and at least one selected from the group consisting of bisphosphonates, active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or antigen binding fragments of the antibodies, anti-PTHrP (parathyroid hormone-related protein) antibodies or antigen binding fragments of the antibodies, IL-1 receptor antagonists, anti-IL-6 receptor antibodies or antigen binding fragments of the antibodies, anti-RANKL antibodies or antigen binding fragments of the antibodies, and OCIF (osteoclastogenesis inhibitory factor).

(10) The pharmaceutical composition according to (8) or (9), wherein the abnormal bone metabolism is selected from the group consisting of osteoporosis, bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, bone Paget's disease, renal osteodystrophy, and osteogenesis imperfecta.

(11) The pharmaceutical composition according to (10), characterized in that the abnormal bone metabolism is osteoporosis, bone destruction accompanying rheumatoid arthritis, or bone destruction accompanying cancer metastasis to bone.

(12) The pharmaceutical composition according to (11), characterized in that the abnormal bone metabolism is osteoporosis.

(13) The pharmaceutical composition according to (12), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(14) A method for the treatment and/or prophylaxis of abnormal bone metabolism, characterized by administering at least one of the antibodies or antigen binding fragments of the antibodies according to (1) to (6) or the pharmaceutical composition according to (8) or (9).

(15) A method for the treatment and/or prophylaxis of abnormal bone metabolism, characterized by simultaneously or successively administering at least one of the antibodies or antigen binding fragments of the antibodies according to (1) to (6) or the pharmaceutical composition according to (8) and at least one selected from the group consisting of bisphosphonates, active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or antigen binding fragments of the antibodies, anti-PTHrP (parathyroid hormone-related protein) antibodies or antigen binding fragments of the antibodies, IL-1 receptor antagonists, anti-IL-6 receptor antibodies or antigen binding fragments of the antibodies, anti-RANKL antibodies or antigen binding fragments of the antibodies, and OCIF (osteoclastogenesis inhibitory factor).

(16) The method for the treatment and/or prophylaxis according to (14) or (15), characterized in that the abnormal bone metabolism is osteoporosis, bone destruction accompanying rheumatoid arthritis, or bone destruction accompanying cancer metastasis to bone.

(17) The method for the treatment and/or prophylaxis according to (16), characterized in that the abnormal bone metabolism is osteoporosis.

(18) The method for the treatment and/or prophylaxis according to (17), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(19) A polynucleotide encoding the antibody according to any one of (1) to (6).

(20) The polynucleotide according to (19), characterized by comprising a polynucleotide comprising a nucleotide sequence comprising nucleotides 58 to 420 of a nucleotide sequence represented by SEQ ID NO: 5 and a polynucleotide comprising a nucleotide sequence comprising nucleotides 61 to 399 of a nucleotide sequence represented by SEQ ID NO: 3.

(21) The polynucleotide according to (19), characterized by comprising a polynucleotide comprising a nucleotide sequence comprising nucleotides 58 to 1398 of a nucleotide sequence represented by SEQ ID NO: 5 and a polynucleotide comprising a nucleotide sequence comprising nucleotides 61 to 714 of a nucleotide sequence represented by SEQ ID NO: 3.

(22) A vector, comprising any one of the polynucleotides according to (19) to (21).

(23) A transformed host cell, comprising any one of the polynucleotides according to (19) to (21).

(24) A transformed host cell, comprising the vector according to (22).

(25) A method of producing the antibody according to any one of (1) to (6), comprising culturing the host cell according to (23) or (24), and purifying an antibody from the resulting culture product.

Effects of Invention

According to the invention, a therapeutic and/or prophylactic agent for abnormal bone metabolism, whose mechanism of action is to inhibit the differentiation and maturation of osteoclasts and the bone resorption activity thereof, can be obtained.

BRIEF DESCRIPTION OF DRAWINGS

FIG. 1 shows a nucleotide sequence of a K3-1115 antibody heavy chain and an amino acid sequence thereof.
FIG. 2 shows a nucleotide sequence of a K3-1115 antibody light chain and an amino acid sequence thereof.
FIG. 3 shows a nucleotide sequence of a K3-1115/T103E antibody heavy chain and an amino acid sequence thereof. Incidentally, the K3-1115/T103E antibody light chain and the K3-1115 antibody light chain are the same as each other.
FIG. 4 shows the amino acid sequences of the respective CDRs of a #32A1 antibody and the K3-1115/T103E antibody.
FIG. 5 shows a graph depicting the inhibition of the bone resorption activity of normal human osteoclasts by the addition of the K3-1115/T103E antibody (N=6).

DESCRIPTION OF EMBODIMENTS

The term "gene" as used herein includes not only DNA, but also mRNA, cDNA, and cRNA.
The term "polynucleotide" as used herein is used with the same meaning as a "nucleic acid" and also includes DNA, RNA, probes, oligonucleotides, and primers.
The terms "polypeptide" and "protein" as used herein are used without distinction.
The term "RNA fraction" as used herein refers to a fraction containing RNA.
The term "cell" as used herein includes cells in an animal individual and cultured cells.
The term "Siglec-15" as used herein is used with the same meaning as "Siglec-15 protein".
The term "osteoclast formation" as used herein is used with the same meaning as "osteoclast differentiation" or "osteoclast maturation".
The term "antigen binding fragment of an antibody" as used herein is used with the same meaning as "functional fragment of an antibody" and refers to a partial fragment of an antibody having an activity of binding to an antigen and includes Fab, F(ab')2, Fv, scFv, diabodies, linear antibodies, polyspecific antibodies formed from antibody fragments, and the like. The term also encompasses Fab' which is a monovalent fragment in a variable region of an antibody obtained by treating F(ab')2 under reducing conditions. However, the term is not limited to these molecules as long as the fragment has a binding affinity for an antigen. Further, these antigen binding fragments include not only a fragment obtained by treating a full-length molecule of an antibody protein with an appropriate enzyme, but also a protein produced in an appropriate host cell using a genetically modified antibody gene.

It is known that each heavy and light chain of an antibody molecule has three complementarity determining regions (CDRs). The complementarity determining region is also called the hypervariable domain, and is present in a variable region of each heavy and light chain of an antibody. It is a site which has particularly high variability in its primary structure, and there are three separate CDRs in the primary structure of each heavy and light polypeptide chain. In this specification, as for the complementarity determining regions of an antibody, the complementarity determining regions of the heavy chain are represented by CDRH1, CDRH2, and CDRH3 from the amino-terminal end of the amino acid sequence of the heavy chain, and the complementarity determining regions of the light chain are represented by CDRL1, CDRL2, and CDRL3 from the amino-terminal end of the amino acid sequence of the light chain. These sites are proximate to one another in the tertiary structure and determine the specificity for an antigen to which the antibody binds.

The phrase "hybridization is performed under stringent conditions" as used herein refers to hybridization being performed under conditions under which identification can be achieved by performing hybridization at 68° C. in a commercially available hybridization solution, ExpressHyb Hybridization Solution (manufactured by Clontech Laboratories, Inc.) or performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. Siglec-15

The present inventors have found that the Siglec-15 gene is specifically expressed in giant cell tumors and have also found that the expression level of the Siglec-15 gene increases when a monocyte-derived cell line differentiates into osteoclasts.

Siglec-15 to be used in the invention is directly purified from monocytes or bone marrow cells of a human, non-human mammal (such as a guinea pig, rat, mouse, rabbit, pig, sheep, cattle, or monkey) or chicken and can then be used, or is prepared from a cell membrane fraction of the above-mentioned cells and can then be used. Further, Siglec-15 can be obtained by in vitro synthesis or production in a host cell through genetic engineering. Specifically, in such genetic engineering production, Siglec-15 cDNA is integrated into a vector capable of expressing Siglec-15 cDNA, and Siglec-15 is synthesized in a solution containing enzymes, substrates, and energy substances required for transcription and translation, or another prokaryotic or eukaryotic host cell is transformed to express Siglec-15, whereby the protein can be obtained.

The nucleotide sequence of human Siglec-15 cDNA has been registered in GenBank with an accession number of NM_213602. The nucleotide sequence of mouse Siglec-15 cDNA has been registered in GenBank with an accession number of XM_884636. Incidentally, Siglec-15 is sometimes called CD33 antigen-like 3, CD33 molecule-like 3, CD33-like 3, or CD33L3, and all of these represent the same molecule.

Siglec-15 cDNA can be obtained by, for example, a so-called PCR method in which a polymerase chain reaction (hereinafter referred to as "PCR") is performed using a cDNA library expressing Siglec-15 cDNA as a template and primers which specifically amplify Siglec-15 cDNA (Saiki, R. K., et al., Science, (1988) 239, 487-49).

Incidentally, a polynucleotide which hybridizes to a polynucleotide comprising a nucleotide sequence complementary to a nucleotide sequence encoding human or mouse Siglec-15 under stringent conditions and encodes a protein having a biological activity comparable to that of Siglec-15 is also regarded as Siglec-15 cDNA. Further, a polynucleotide which is a splicing variant transcribed from the human or mouse Siglec-15 locus or a polynucleotide which hybridizes to a sequence complementary thereto under stringent conditions and encodes a protein having a biological activity comparable to that of Siglec-15 is also regarded as Siglec-15 cDNA.

Further, a protein which comprises an amino acid sequence including substitution, deletion or addition of one or several amino acids in an amino acid sequence of human or mouse Siglec-15 or an amino acid sequence obtained by removing the signal sequence from this sequence and which has a biological activity comparable to that of Siglec-15 is also regarded as Siglec-15. Further, a protein which comprises an amino acid sequence encoded by a splicing variant transcribed from the human or mouse Siglec-15 locus or an amino acid sequence including substitution, deletion or addition of one or several amino acids therein and which has a biological activity comparable to that of Siglec-15 is also regarded as Siglec-15.

2. Detection of Abnormal Bone Metabolism

An analysis of the expression level of the Siglec-15 gene in a group of test samples from various human bone tissues showed that the expression level of the gene significantly increases in giant cell tumor (GCT) which is a bone tumor with a large number of osteoclast-like multinucleated giant cells arising and is characterized by clinical findings of osteolytic bone destruction (Bullough et al., Atlas of Orthopedic Pathology 2nd edition, pp. 17.6-17.8, Lippincott Williams & Wilkins Publishers (1992)).

It was also found that the expression level of the Siglec-15 gene increases when a monocyte-derived cell line is differentiated into osteoclasts.

Accordingly, Siglec-15 is considered to be associated with human pathologies such as GCT in which bone resorption is increased. In other words, measurement of the expression level of the Siglec-15 gene and/or Siglec-15 in each cell and/or each tissue enables determination of the state of abnormal bone metabolism accompanied by over-expression of Siglec-15. The term "abnormal bone metabolism" as used herein refers to a disorder characterized by net bone loss, and specific examples thereof include, but are not limited to, osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, bone Paget's disease, renal osteodystrophy, and osteogenesis imperfecta.

In the invention, the "test sample" to be used for examining the expression level of the Siglec-15 gene and/or Siglec-15 refers to a sample of tissue from bone marrow, bone, prostate, testis, penis, bladder, kidney, oral cavity, pharynx, lip, tongue, gingiva, nasopharynx, esophagus, stomach, small intestine, large intestine, colon, liver, gallbladder, pancreas, nose, lung, soft tissue, skin, breast, uterus, ovary, brain, thyroid, lymph node, muscle, fat tissue or the like, or blood, a body fluid, an excretion, or the like obtained from a test subject, a clinical specimen, etc., however, in the invention, blood or bone marrow is more preferred.

As regards RANKL, which is known to be associated with osteoclast differentiation, a knockout mouse has been produced, and the phenotype when the function of RANKL has been lost has been analyzed (Young-Yun Kong, et. al., Nature (1999) 397, pp. 315-323). By producing a knockout mouse devoid of Siglec-15 in the same manner as above, the phenotype when the function of Siglec-15 has been lost can be analyzed.

3. Production of Anti-Siglec-15 Antibody

The antibody of the invention, which is against Siglec-15, can be obtained by immunizing an animal with Siglec-15 or an arbitrary polypeptide selected from the amino acid sequence of Siglec-15, and collecting and purifying the antibody produced in vivo according to common procedures. The biological species of Siglec-15 to be used as an antigen is not limited to being human, and an animal can be immunized with Siglec-15 derived from an animal other than humans such as a mouse or a rat. In this case, by examining the cross-reactivity between an antibody binding to the obtained heterologous Siglec-15 and human Siglec-15, an antibody applicable to a human disease can be selected.

Further, a monoclonal antibody can be obtained by fusing antibody-producing cells which produce an antibody against Siglec-15 with myeloma cells to establish a hybridoma according to a known method (for example, Kohler and Milstein, Nature, (1975) 256, pp. 495-497; Kennet, R. ed., Monoclonal Antibodies, pp. 365-367, Plenum Press, N.Y. (1980)). A specific example of such a method is described in WO 09/48072 (published on Apr. 16, 2009) and WO 10/117011 (published on Oct. 14, 2010).

Incidentally, Siglec-15 to be used as an antigen can be obtained by genetic engineering whereby a host cell is caused to express the Siglec-15 gene. Specifically, a vector capable of expressing the Siglec-15 gene is produced, and the resulting vector is transfected into a host cell to express the gene, and then the expressed Siglec-15 is purified.

Examples of the hybridoma strain thus established include hybridoma #32A1 described in WO 09/48072. The hybridoma #32A1 was deposited at the International Patent Organism Depository of the National Institute of Advanced Industrial Science and Technology (located at Central 6, 1-1-1 Higashi, Tsukuba-shi, Ibaraki-ken, 305-8566, Japan) on Aug. 28, 2008, and has been given an accession number of FERM BP-10999 under the name of anti-Siglec-15 Hybridoma #32A1. Incidentally, in this specification, the antibody produced by the hybridoma #32A1 is referred to as the "#32A1 antibody" or simply "#32A1". A partial fragment containing the heavy chain variable region or the light chain variable region of the #32A1 antibody is described in WO 2010/117011.

By artificially modifying the sequence of the above-mentioned monoclonal antibody against Siglec-15 for the purpose of decreasing heterologous antigenicity to humans or the like, a humanized antibody, which is a recombinant antibody, can be produced. The antibody of the invention includes an antibody in which a CDR of the above-mentioned humanized antibody is modified. These antibodies can be produced using known methods.

As the humanized antibody, an antibody obtained by integrating only complementarity determining regions (CDRs) into a human-derived antibody (see Nature (1986) 321, pp. 522-525), and an antibody obtained by grafting part of the amino acid residues of the framework as well as the CDR sequences to a human antibody by a CDR-grafting method (WO 90/07861) can be exemplified. As an example of a humanized antibody of a rat antibody #32A1, a combination of a heavy chain containing a heavy chain variable region comprising an amino acid sequence comprising amino acid residues 20 to 140 of SEQ ID NO: 2 and a light chain containing a light chain variable region comprising an amino acid sequence comprising amino acid residues 21 to 133 of SEQ ID NO: 4 can be exemplified.

Further, as a preferred antibody, an antibody comprising a heavy chain having an amino acid sequence comprising amino acid residues 20 to 466 of SEQ ID NO: 2 and a light chain having an amino acid sequence comprising amino acid residues 21 to 238 of SEQ ID NO: 4 can be exemplified. In this specification, the above-mentioned antibody is referred to as "K3-1115" or "K3-1115 antibody".

However, the humanized antibody derived from the #32A1 antibody is not limited to the above-mentioned humanized antibodies as long as the humanized antibody has all 6 types of CDR sequences of #32A1 and has the activity of inhibiting osteoclast formation. Incidentally, the heavy chain variable region of the #32A1 antibody has CDRH1 (DYFMN) comprising an amino acid sequence represented by SEQ ID NO: 7, either one of CDRH2 (QIRNKIYTYAT-FYAESLEG) comprising an amino acid sequence represented by SEQ ID NO: 8 and CDRH2 (QIRNKIYTYAT-FYA) represented by SEQ ID NO: 9, and CDRH3 (SLTGGDYFDY) comprising an amino acid sequence represented by SEQ ID NO: 10. The CDRH2 represented by SEQ ID NO: 8 is in accordance with the Kabat definition (SEQUENCES OF PROTEINS OF IMMUNOLOGICAL INTEREST VOL. I, FIFTH EDITION (1991)). The CDRH2 represented by SEQ ID NO: 9 is made shorter by five residues at the C terminus than the Kabat definition. In the heavy chain sequence containing this CDRH2, the CDR sequence derived from a rat is made shorter and more of a human framework sequence is incorporated, and therefore, when it is administered to humans, it is much less likely to be recognized as a heterologous antigen. Further, the light chain variable region of the #32A1 antibody has CDRL1 (RASQSVTISGYSFIH) comprising an amino acid sequence represented by SEQ ID NO: 12, CDRL2 (RASNLAS) comprising an amino acid sequence represented by SEQ ID NO: 13, and CDRL3 (QQSRKSPWT) comprising an amino acid sequence represented by SEQ ID NO: 14. Incidentally, the amino acid sequences of the above-mentioned CDRs of SEQ ID NOS: 7 to 10, and 12 to 14 are also shown in FIG. 4.

As one example of the CDR-modified variant of the humanized antibody derived from the #32A1 antibody, an antibody in which a threonine residue at position 3 of the CDRH3 of SEQ ID NO: 10 has been substituted with a glutamic acid residue can be exemplified. Siglec-15 is a basic protein, and by introducing an acidic amino acid residue such as aspartic acid or glutamic acid into the antibody sequence, an ionic bond is formed between the antigen and the antibody, and thus, the binding affinity is expected to be improved. A substitution variant was designed in which a glutamic acid residue, which is an acidic amino acid and has a long side chain, was introduced into the antibody at the position of a threonine residue which is located in the center of the CDRH3 loop which is considered to be the most important CDR at the antibody recognition site and is presumed to face the antigen based on an X-ray crystal structure analysis. The CDRH3 including the above-mentioned substitution (SLEGGDYFDY) corresponds to an amino acid sequence of SEQ ID NO: 11 in the Sequence Listing. Incidentally, the amino acid sequence of the CDRH3 of SEQ ID NO: 11 is also shown in FIG. 4.

As a preferred example of the above-mentioned CDR-modified variant antibody, a combination of a heavy chain containing a heavy chain variable region comprising an amino acid sequence comprising amino acid residues 20 to 140 of SEQ ID NO: 6 and a light chain containing a light chain variable region comprising an amino acid sequence comprising amino acid residues 21 to 133 of SEQ ID NO: 4 can be exemplified.

As a more preferred antibody, an antibody comprising a heavy chain having an amino acid sequence comprising amino acid residues 20 to 466 of by SEQ ID NO: 6 and a light chain having an amino acid sequence comprising amino acid residues 21 to 238 of SEQ ID NO: 4 can be exemplified. In this specification, the above-mentioned antibody is referred to as "K3-1115/T103E" or "K3-1115/T103E antibody". Incidentally, the K3-1115/T103E antibody heavy chain is a sequence in which a threonine residue at position 103 of an amino acid sequence obtained by removing the signal sequence from the K3-1115 heavy chain sequence represented by SEQ ID NO: 2 has been substituted with a glutamic acid residue.

However, the CDR-modified variant of the humanized #32A1 of the invention is not limited to the above-mentioned CDR-modified variant as long as it has the CDRH3 sequence of SEQ ID NO: 11. Further, the CDRH2 sequence of the CDR-modified variant of the humanized #32A1 of the invention may be CDRH2 represented by either SEQ ID NO: 8 or SEQ ID NO: 9.

Incidentally, it is known that any lysine residue at the carboxyl terminus of the heavy chain of an antibody produced by a mammalian cultured cell is deleted (Journal of Chromatography A, 705: 129-134 (1995)), and it is also known that the following two amino acid residues: glycine and lysine at the carboxyl terminus of such a heavy chain are deleted, and any proline residue located at the carboxyl terminus is newly amidated (Analytical Biochemistry, 360: 75-83 (2007)). However, such deletion and modification of the heavy chain sequence do not affect the antigen binding affinity and effector function (complement activation, antibody-dependent cytotoxic activity, etc.) of the antibody. Therefore, the invention also includes an antibody subjected to such modifications, and a deletion variant in which one or two amino acids at the carboxyl terminus of the heavy chain have been deleted, a deletion variant obtained by amidation of the same (for example, a heavy chain in which a proline residue at the carboxyl-terminal site has been amidated), and the like can be exemplified. However, a deletion variant in which a carboxyl-terminal residue of the heavy chain of the antibody according to the invention has been deleted is not limited to the above-mentioned variants as long as it has antigen binding affinity and effector function. The two heavy chains constituting the antibody according to the invention may comprise a full-length heavy chain and any one heavy chain selected from the group consisting of the above-mentioned deletion variants, or may comprise any two heavy chains selected therefrom in combination. The relative amount of each deletion variant can be affected by the type of mammalian cultured cell used in production of the antibody according to the invention and the culture conditions, however, one example is where, as the main component of the antibody according to the invention, both of the two heavy chains include deletion of one amino acid residue at the carboxyl terminus.

The antibodies obtained by the above method can be evaluated for binding activity to an antigen by the method described in Example 3 or the like, and a preferred antibody can be selected. As one example of another index by which the properties of antibodies are compared, the stability of antibodies can be exemplified. Differential scanning calorimetry (DSC) is a method capable of rapidly and accurately measuring a thermal denaturation midpoint temperature (Tm) which is a favorable index of relative structural stability of proteins. By measuring Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies are as follows: the yield in an appropriate host cell is high; and the aggregability in an aqueous solution is low. For example, an antibody which shows the highest yield does not always show high thermal stability, and therefore, it is necessary to select an antibody most suitable for administering to humans by making a comprehensive evaluation based on the above-mentioned indices.

Further, a method in which the full-length heavy and light chain sequences of an antibody are ligated using an appropriate linker, whereby a single-chain immunoglobulin is obtained is also known (Lee, H-S, et. al., Molecular Immunology (1999) 36, pp. 61-71; Shirrmann, T. et. al., mAbs (2010), 2, (1) pp. 1-4). By dimerizing such a single-chain immunoglobulin, the resulting dimer can have a structure and an activity similar to those of an antibody which is a tetramer itself. Further, the antibody of the invention may be an antibody which has a single heavy chain variable region and does not have a light chain sequence. Such an antibody is called a single domain antibody (sdAb) or a nanobody, and in fact, it is observed in camels and llamas and has been reported to have antigen binding affinity (Muyldemans S. et. al., Protein Eng. (1994) 7(9), 1129-35, Hamers-Casterman C. et. al., Nature (1993) 363 (6428) 446-8). The above-mentioned antibodies can also be regarded as a type of antigen binding fragment of the antibody according to the invention.

Further, by controlling glycosylation in which a glycan is bound to the antibody of the invention, it is possible to enhance antibody-dependent cytotoxic activity. As regards techniques for controlling the glycosylation of antibodies, WO 99/54342, WO 00/61739, WO 02/31140, etc. are known. However, the techniques are not limited thereto.

In cases where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately. In cases where eukaryotic cells are used as the host, animal cells, plant cells, and eukaryotic microorganisms can be used. As the animal cells, mammalian cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61) can be exemplified. Further, in cases where prokaryotic cells are used, for example, *Escherichia coli* and *Bacillus subtilis* can be exemplified. By introducing a target antibody gene into these cells through transformation, and culturing the thus transformed cells in vitro, the antibody can be obtained. In the above-mentioned culture method, the yield may sometimes vary depending on the sequence of the antibody, and therefore, it is possible to select one which is easily produced as a pharmaceutical by using the yield as an index among the antibodies having a comparable binding activity.

There is no limitation to the isotype of the antibody of the invention, and examples thereof include IgG (IgG1, IgG2, IgG3, IgG4), IgM, IgA (IgA1, IgA2), IgD, and IgE, and preferred examples thereof include IgG and IgM, and further more preferred examples thereof include IgG1 and IgG2.

Further, the antibody of the invention may be an antigen binding fragment of the antibody having an antigen binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or some of the functions of the full-length molecule of the antibody can be called an antigen binding fragment of the antibody. As the functions of the antibody, generally an antigen binding activity, an activity of neutralizing the activity of an antigen, an activity of increasing the activity of an antigen, an antibody-dependent cytotoxic activity, a complement-dependent cytotoxic activity, and a complement-dependent cellular cytotoxic activity can be exemplified. The function of the antigen binding fragment of the antibody according to the invention is binding activity to Siglec-15, preferably the activity of inhibiting the formation of osteoclasts, more preferably the activity of inhibiting the process of cell fusion of osteoclasts.

Examples of the fragment of the antibody include Fab, F(ab')2, Fv, single-chain Fv (scFv) in which Fv molecules of the heavy chain and the light chain are ligated via an appropriate linker, a diabody (diabodies), a linear antibody, and a polyspecific antibody composed of the antibody fragment. Further, Fab' which is a monovalent fragment in a variable region of an antibody obtained by treating F(ab')2 under reducing conditions is also regarded as a fragment of the antibody.

Further, the antibody of the invention may be a polyspecific antibody with specificity for at least two different antigens. In general, such a molecule binds to two antigens (that is, a bispecific antibody), however, the "polyspecific antibody" as used herein includes an antibody having specificity for two or more (for example, three) antigens.

The polyspecific antibody of the invention may be a full-length antibody or a fragment of such an antibody (for example, a F(ab')2 bispecific antibody). The bispecific antibody can be produced by ligating the heavy and light chains (HL pairs) of two types of antibodies, or can also be produced by fusing hybridomas which produce different monoclonal antibodies to prepare bispecific antibody-producing fused cells (Millstein et al., Nature (1983) 305, pp. 537-539).

The antibody of the invention may be a single-chain antibody (also referred to as scFv). The single-chain antibody can be obtained by ligating the heavy chain variable region and the light chain variable region of an antibody via a polypeptide linker (Pluckthun, The Pharmacology of Monoclonal Antibodies, 113 (edited by Rosenburg and Moore, Springer Verlag, New York, pp. 269-315 (1994), Nature Biotechnology (2005), 23, pp. 1126-1136). Further, a BiscFv fragment produced by ligating two scFv molecules via a polypeptide linker can also be used as the bispecific antibody.

Methods of producing a single-chain antibody are known in this technical field (see, for example, U.S. Pat. Nos. 4,946,778, 5,260,203, 5,091,513, 5,455,030, etc.). In this scFv, the heavy chain variable region and the light chain variable region are ligated via a linker which does not form a conjugate, preferably via a polypeptide linker (Huston, J. S. et al., Proc. Natl. Acad. Sci. USA (1988), 85, pp. 5879-5883). In the scFv, the heavy chain variable region and the light chain variable region may be derived from the same antibody or different antibodies. As the polypeptide linker to be used for ligating the variable regions, for example, a given single-chain peptide composed of 12 to 19 residues is used.

DNA encoding scFv can be obtained by performing amplification using a DNA encoding the entire amino acid sequence, or a desired partial amino acid sequence, selected from the heavy chain or the heavy chain variable region of the above-mentioned antibody and the light chain or the light chain variable region thereof as a template by a PCR method using a primer pair that defines both ends thereof, and further performing amplification by combining a DNA encoding a polypeptide linker portion and a primer pair that defines both ends thereof so as to ligate both of the ends to the heavy chain and the light chain, respectively.

Further, once DNA encoding scFv is produced, an expression vector containing the same and a host transformed by the expression vector can be obtained according to common procedures. Further, by using the resulting host, scFv can be obtained according to common procedures. An antibody fragment thereof can be produced in a host by obtaining a gene and expressing the gene in the same manner as described above.

The antibody of the invention may be multimerized to increase its affinity for an antigen. The antibody to be multimerized may be one type of antibody or a plurality of antibodies which recognize a plurality of epitopes of the same antigen. As a method of multimerization of the antibody, binding of the IgG CH3 domain to two scFv molecules, binding to streptavidin, introduction of a helix-turn-helix motif and the like can be exemplified.

The antibody of the invention may be a polyclonal antibody which is a mixture of plural types of anti-Siglec-15 antibodies having different amino acid sequences. As one example of the polyclonal antibody, a mixture of plural types of antibodies having different CDRs can be exemplified. As such a polyclonal antibody, a mixture of cells which produce different antibodies is cultured, and an antibody purified from the resulting culture can be used (see WO 2004/061104).

An antibody bound to any of various types of molecules such as polyethylene glycol (PEG) as a modifying substance of the antibody can also be used.

Further, the antibody of the invention may be in the form of a conjugate formed between any of these antibodies and another medicinal agent (an immunoconjugate). Examples of such an antibody include one in which the antibody is conjugated to a radioactive material or a compound having a pharmacological effect (Nature Biotechnology (2005) 23, pp. 1137-1146).

The obtained antibody can be purified to homogeneity. The separation and purification of the antibody can be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography. Such chromatography can be performed employing liquid chromatography such as HPLC or FPLC. As a column to be used in affinity chromatography, a Protein A column and a Protein G column can be exemplified. For example, as a column using a Protein A column, Hyper D, POROS, Sepharose FF (Pharmacia) and the like can be exemplified. Further, by using a carrier having an antigen immobilized thereon, the antibody can also be purified utilizing the binding activity of the antibody to the antigen.

4. Medicament Containing Anti-Siglec-15 Antibody

From the anti-Siglec-15 antibodies obtained by the method described in the above section "3. Production of anti-Siglec-15 antibody", an antibody which neutralizes the biological activity of Siglec-15 can be obtained. Such an antibody which neutralizes the biological activity of Siglec-15 inhibits the biological activity of Siglec-15 in vivo, i.e., the differentiation and/or maturation of osteoclasts, and therefore can be used as a therapeutic and/or prophylactic agent for abnormal bone metabolism caused by abnormal differentiation and/or maturation of osteoclasts as a medicament. The abnormal bone metabolism may be any disorder characterized by net bone loss (osteopenia or osteolysis). In general, the treatment and/or prophylaxis by the anti-Siglec-15 antibody are/is applied to a case where inhibition of bone resorption is required. Examples of the abnormal bone metabolism which can be treated and/or prevented by the anti-Siglec-15 antibody include osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, bone Paget's disease, renal osteodystrophy, and osteogenesis imperfecta, however, the abnormal bone metabolism is not limited thereto as long as it is a disease accompanied by net bone loss caused by osteoclasts. Examples of the anti-Siglec-15 antibody to be used as the above-mentioned medicament include a humanized antibody produced from the #32A1 antibody, and a CDR-modified antibody thereof.

The in vitro activity of the anti-Siglec-15 antibody of neutralizing the biological activity of Siglec-15 can be determined by, for example, the activity of inhibiting the differentiation of the cells which overexpress Siglec-15 into osteoclasts. For example, the anti-Siglec-15 antibody is added to a mouse monocyte-derived cell line RAW 264.7 cells or RAW 264 cells at various concentrations, and the activity of inhibiting the differentiation into osteoclasts by stimulation with RANKL or TNF-α can be determined. Further, the anti-Siglec-15 antibody is added to bone marrow-derived primary cultured cells at various concentrations, and the activity of inhibiting the differentiation into osteoclasts by stimulation with RANKL, TNF-α, or active vitamin $D_3$ can be determined. Further, the anti-Siglec-15 antibody is added to normal human osteoclast precursor cells (Normal Human Natural Osteoclast Precursor Cells, available from Sanko Junyaku Co., Ltd., Cat. No. 2T-110) at various concentrations, and the activity of inhibiting the differentiation into osteoclasts by stimulation with RANKL and M-CSF can be determined. Such an inhibitory effect on osteoclast differentiation can be determined by using the inhibition of tartrate-resistant acid phosphatase (TRAP) activity of osteoclasts as an index. Further, the inhibitory effect on osteoclast differentiation can also be determined by using the inhibition of formation of TRAP-positive multinucleated osteoclasts, i.e., the inhibition of cell fusion of osteoclasts as an index. Further, in an experiment utilizing a pit assay (Takada et al., Bone and Mineral, (1992) 17, 347-359) using femur- and/or tibia-derived cells, the in vitro activity of inhibiting the bone resorption by osteoclasts can be determined by adding the anti-Siglec-15 antibody to femur- and/or tibia-derived cells at various concentrations, and observing pit formation on a dentine slice. As a system for determining the in vitro activity of inhibiting the bone resorption by osteoclasts, it is also possible to use a plate coated with europium-conjugated human collagen. The in vivo therapeutic or prophylactic effect of the anti-Siglec-15 antibody on abnormal bone metabolism using an experimental animal can be confirmed by, for example, administering the anti-Siglec-15 antibody to an animal model of osteoporosis or a transgenic animal which overexpresses Siglec-15 and measuring any change in osteoclasts. Examples of the animal model of osteoporosis are ovariectomized rats and ovariectomized monkeys. The inhibitory effect of the anti-Siglec-15 antibody on bone resorption activity can be determined by administering the anti-Siglec-15 antibody to such an experimental animal, and then, measuring a bone mineral density or a bone metabolism marker. Examples of the bone metabolism marker include, but are not limited to, bone resorption markers such as urinary deoxypyridinoline, urinary N-telopeptide of type I collagen (NTX), urinary C-telopeptide of type I collagen (CTX), blood NTX, blood CTX, and blood tartrate-resistant acid phosphatase (TRAP5b), and bone formation markers such as blood bone alkaline phosphatase (BAP), blood osteocalcin (BGP), and procollagen type I C-peptide (P1NP).

The obtained antibody, which neutralizes the biological activity of Siglec-15, is useful as a medicament, particularly as a pharmaceutical composition for the treatment or prophylaxis of abnormal bone metabolism such as osteoporosis, bone destruction accompanying rheumatoid arthritis, or bone destruction accompanying cancer metastasis to bone, or as an antibody for immunological diagnosis of such disease.

In the treatment of rheumatoid arthritis (RA), a major problem is bone loss accompanying the occurrence of the disease. It has been reported that osteoclasts play a primary role in this bone loss accompanying RA. The cytokines considered to be the most important as the cause of osteoclast induction (differentiation and maturation), and activation and in bone destruction in RA are RANKL and TNF-α (Romas E. et al., Bone 30, pp. 340-346, 2002). OCIF/OPG, which is a decoy receptor for RANKL, can inhibit osteoclast formation induced by RANKL but it does not inhibit osteoclast formation induced by TNF-α. On the other hand, the anti-Siglec-15 antibody according to the invention effectively inhibited osteoclast formation induced by both RANKL and TNF-α. Therefore, it is expected that the anti-Siglec-15 antibody of the invention can inhibit bone loss and bone destruction induced by TNF-α in RA, or the like, more strongly than an RANKL blocker (OCIF/OPG, an anti-RANKL antibody, or the like).

As one example, for the treatment or prophylaxis of abnormal bone metabolism, the anti-Siglec-15 antibody can be administered alone or in combination with at least one other therapeutic agent for a bone disease. As another example, the anti-Siglec-15 antibody can be administered in combination with a therapeutically effective amount of a therapeutic agent for abnormal bone metabolism. Examples of the other therapeutic agent which can be administered in combination with the anti-Siglec-15 antibody include, but are not limited to: bisphosphonates (for example, alendronate, etidronate, ibandronate, incadronate, pamidronate, risedronate, and zoledronate), active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents (for example, celecoxib and rofecoxib), soluble TNF receptors (for example, etanercept), anti-TNF-α antibodies or antigen binding fragments of the antibodies (for example, infliximab), anti-PTHrP (parathyroid hormone-related protein) antibodies or antigen binding fragments of the antibodies, IL-1 receptor antagonists (for example, anakinra), anti-IL-6 receptor antibodies or antigen binding fragments of the antibodies (for example, tocilizumab), anti-RANKL antibodies or antigen binding fragments of the antibodies (for example, denosumab), and OCIF (osteoclastogenesis inhibitory factor). Depending on the state of abnormal bone metabolism and/or the intended degree of the treatment and/or prophylaxis, two or three, or more types of other therapeutic agents can be administered, and these other therapeutic agents can be administered all together by encapsulating them in the same preparation. The other therapeutic agents and the anti-Siglec-15 antibody can also be administered all together by encapsulating them in the same preparation. In addition, the anti-Siglec-15 antibody and the other therapeutic agents can also be administered all together by encapsulating them in separate preparations. Further, the other therapeutic agents and the anti-Siglec-15 antibody can also be separately administered successively, that is, after the other therapeutic agents are administered, a therapeutic agent containing the anti-Siglec-15 antibody or an antigen binding fragment of the antibody as an active ingredient may be administered, or after a therapeutic agent containing the anti-Siglec-15 antibody or an antigen binding fragment of the antibody as an active ingredient is administered, the other therapeutic agents may be administered. In the case of administration in gene therapy, a gene of a proteinous therapeutic agent for a bone disease and a gene of the anti-Siglec-15 antibody can be inserted downstream of the same promoter region or different promoter regions, and can be introduced into the same vector or different vectors.

By conjugating a therapeutic agent for a bone disease to the anti-Siglec-15 antibody or a fragment thereof, a targeted drug conjugate as described in M. C. Garnet "Targeted drug conjugates: principles and progress", Advanced Drug Delivery Reviews, (2001) 53, 171-216 can be produced. For achieving this purpose, other than the antibody molecule, any antibody fragment can be applied as long as it does not completely lose the ability to recognize osteoclasts, and examples thereof include fragments such as Fab, F(ab')2, and Fv. In the invention, the antibody and the fragment can be used in the same manner. The conjugate formed by the anti-Siglec-15 antibody or a fragment thereof and a therapeutic agent for a bone disease can be any of various forms described in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123 and the like. For example, a conjugate in which the anti-Siglec-15 antibody and a therapeutic agent for a bone disease are conjugated to each other chemically and directly or via a spacer such as an oligopeptide and a conjugate formed via an appropriate drug carrier. Examples of the drug carrier include a liposome and a water-soluble polymer. More specific examples of the conjugate formed via such a drug carrier include a conjugate in which a therapeutic agent for a bone disease are incorporated in a liposome and the liposome and the antibody are conjugated to each other, and a conjugate in which a therapeutic agent for a bone disease is conjugated to a water-soluble polymer (a compound having a molecular weight of about 1,000 to 100,000) chemically and directly or via a spacer such as an oligopeptide and the antibody is conjugated to the water-soluble polymer. The conjugation of the antibody (or a fragment thereof) to a therapeutic agent for a bone disease or a drug carrier such as a liposome or a water-soluble polymer can be effected by a method known to those skilled in the art such as the method described in G. T. Hermanson "Bioconjugate Techniques" Academic Press, California (1996), Putnam and J. Kopecek "Polymer Conjugates with Anticancer Activity" Advances in Polymer Science (1995) 122, 55-123. The incorporation of a therapeutic agent for a bone disease in a liposome can be effected by a method known to those skilled in the art such as the method described in D. D. Lasic "Liposomes: From Physics to Applications" Elsevier Science Publishers B. V., Amsterdam (1993) or the like. The conjugation of a therapeutic agent for a bone disease to a water-soluble polymer can be effected by a method known to those skilled in the art such as the method described in D. Putnam and J. Kopecek "Polymer Conjugates with Anticancer Activity" Advances in Polymer Science (1995) 122, 55-123. A conjugate of the antibody (or a fragment thereof) and a proteinous therapeutic agent for a bone disease (or a fragment thereof) can be produced by a method known to those skilled in the art through genetic engineering other than the above-mentioned method.

The invention also provides a pharmaceutical composition containing a therapeutically and/or prophylactically effective amount of the anti-Siglec-15 antibody and a pharmaceutically acceptable diluent, carrier, solubilizing agent, emulsifying agent, preservative, and/or adjuvant.

The invention also provides a pharmaceutical composition containing a therapeutically and/or prophylactically effective amount of the anti-Siglec-15 antibody, a therapeutically and/or prophylactically effective amount of at least one therapeutic agent for a bone disease, and a pharmaceutically acceptable diluent, carrier, solubilizing agent, emulsifying agent, preservative, and/or adjuvant. Examples of the therapeutic agent for a bone disease include, but are not limited to, bisphosphonates (for example, alendronate, etidronate, ibandronate, incadronate, pamidronate, risedronate, and zoledronate), active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents (for example, celecoxib and rofecoxib), soluble TNF receptors (for example, etanercept), anti-TNF-α antibodies or antigen binding fragments of the antibodies (for example, infliximab), anti-PTHrP (parathyroid hormone-related protein) antibodies or antigen binding fragments of the antibodies, IL-1 receptor antagonists (for example, anakinra), anti-IL-6 receptor antibodies or antigen binding fragments of the antibodies (for example, tocilizumab), anti-RANKL antibodies or antigen binding fragments of the antibodies (for example, denosumab) and OCIF (osteoclastogenesis inhibitory factor).

The substance to be used in a preparation acceptable in the pharmaceutical composition according to the invention is preferably non-toxic to a person to whom the pharmaceutical composition is to be administered in terms of the dose and concentration.

The pharmaceutical composition of the invention can contain a substance for pharmaceutical use which is capable of changing or maintaining the pH, osmotic pressure, viscosity, transparency, color, isotonicity, aseptic condition, stability, solubility, release rate, absorption rate, or permeability thereof. Examples of such a substance for pharmaceutical use include, but are not limited to, amino acids such as glycine, alanine, glutamine, asparagine, arginine, and lysine; antimicrobial agents; antioxidants such as ascorbic acid, sodium sulfate, and sodium hydrogen sulfite; buffers such as phosphate, citrate, borate buffers, sodium hydrogen carbonate, and Tris-HCl solutions; fillers such as mannitol and glycine; chelating agents such as ethylenediamine tetraacetate (EDTA); complexing agents such as caffeine, polyvinylpyrrolidine, β-cyclodextrin, and hydroxypropyl-β-cyclodextrin; expanders such as glucose, mannose, and dextrin; other carbohydrates such as monosaccharides and disaccharides; coloring agents; flavors; diluents; emulsifying agents; hydrophilic polymers such as polyvinylpyrrolidine; preservatives such as low molecular weight polypeptides, salt forming counter ions, benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates (such as polysorbate 20 and polysorbate 80), Triton, tromethamine, lecithin, and cholesterol; stability enhancing agents such as sucrose and sorbitol; elasticity enhancing agents such as sodium chloride, potassium chloride, and mannitol and sorbitol; transport agents; excipients; and/or pharmaceutical adjuvants. The amount of these substances to be added for pharmaceutical use is preferably from 0.01 to 100 times, particularly preferably from 0.1 to 10 times, the weight of the anti-Siglec-15 antibody. Those skilled in the art can appropriately determine a preferred formulation of the pharmaceutical composition in a preparation depending on the disease to which the composition is applied, the route of administration to be applied, or the like.

The excipient or carrier in the pharmaceutical composition may be in the form of a liquid or a solid. An appropriate excipient or carrier may be injectable water, physiological saline, an artificial cerebral spinal fluid, or another substance commonly used for parenteral administration. Further, neutral physiological saline or physiological saline containing serum albumin can also be used as a carrier. The pharmaceutical composition may contain a Tris buffer at pH 7.0 to 8.5, an acetate buffer at pH 4.0 to 5.5, or a citrate buffer at pH 3.0 to 6.2. Further, such a buffer may be supplemented with sorbitol or other compounds. Examples of the pharmaceutical composition of the invention include a pharmaceutical composition containing the anti-Siglec-15 antibody and a pharmaceutical composition containing the anti-Siglec-15 antibody and at least one therapeutic agent for a bone disease. The pharmaceutical composition of the invention is prepared in the form of a lyophilized product or a liquid as a medicament having a selected composition and a required purity. The pharmaceutical composition containing the anti-Siglec-15 antibody and the pharmaceutical composition containing the anti-Siglec-15 antibody and at least one therapeutic agent for abnormal bone metabolism can also be formed into a lyophilized product using an appropriate excipient such as sucrose.

The pharmaceutical composition of the invention can be prepared for parenteral administration or for gastrointestinal absorption through oral administration. The composition and concentration of the preparation can be determined depending on the administration method. The higher the affinity of the anti-Siglec-15 antibody, contained in the pharmaceutical composition of the invention, is for Siglec-15, that is, the lower the dissociation constant (Kd value) thereof is for Siglec-15, the more the anti-Siglec-15 antibody can exhibit its drug efficacy even when decreasing the dose for humans. Hence, the dose of the pharmaceutical composition of the invention for humans can also be determined based on this consideration. As for the dose, in the case where a human anti-Siglec-15 antibody is administered to humans, the antibody may be administered at a dose of about 0.1 to 100 mg/kg once per one to 180 days.

Examples of the dosage form of the pharmaceutical composition of the invention include injections including infusions, suppositories, transnasal agents, sublingual agents, and percutaneous absorbents.

EXAMPLES

Hereinafter, the invention will be more specifically described with reference to the Examples, however, the invention is not limited thereto. Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, they are used according to the protocols attached thereto unless otherwise stated.

Reference Example 1

Production of Gene of Humanized #32A1 Antibody K3-1115

In this specification, as an antibody to be used as a control in a comparative test, h#32A1-H1-1/L2-15 described in WO 2010/117011 was used. The antibody gene can be produced according to WO 2010/117011. Incidentally, in this specification, the above-mentioned h#32A1-H1-1/L2-15 antibody is referred to as "K3-1115" or "K3-1115 antibody".

The amino acid sequence of the K3-1115 heavy chain is represented by SEQ ID NO: 2 in the Sequence Listing. The sequence comprising amino acid residues 1 to 19 of the amino acid sequence of SEQ ID NO: 2, the sequence comprising amino acid residues 20 to 140 thereof, and the sequence comprising amino acid residues 141 to 466 thereof, correspond to the signal sequence, the heavy chain variable region, and the heavy chain constant region, respectively. A nucleotide sequence encoding the amino acid sequence of SEQ ID NO: 2 is represented by SEQ ID NO: 1 in the Sequence Listing. The sequence comprising nucleotides 1 to 57 of the nucleotide sequence of SEQ ID NO: 1, the sequence comprising nucleotides 58 to 420 thereof, and the sequence comprising nucleotides 421 to 1398 thereof, encode the signal sequence, the heavy chain variable region sequence, and the heavy chain constant region sequence, respectively. The nucleotide sequence of SEQ ID NO: 1 and the amino acid sequence of SEQ ID NO: 2 are shown in FIG. 1.

The amino acid sequence of the K3-1115 light chain is represented by SEQ ID NO: 4 in the Sequence Listing. The sequence comprising amino acid residues 1 to 20 of the amino acid sequence of SEQ ID NO: 4, the sequence comprising amino acid residues 21 to 133 thereof, and the sequence comprising amino acid residues 134 to 238 thereof, correspond to the signal sequence, the light chain variable region, and the light chain constant region, respectively. A nucleotide sequence encoding the amino acid sequence of SEQ ID NO: 4 is represented by SEQ ID NO: 3 in the Sequence Listing. The sequence comprising nucleotides 1 to 60 of the nucleotide sequence of SEQ ID NO: 3, the sequence comprising nucleotides 61 to 399 thereof, and the sequence comprising nucleotides 400 to 714 thereof, encode the signal sequence, the light chain variable region sequence, and the light chain constant region sequence, respectively. The nucleotide sequence of SEQ ID NO: 3 and the amino acid sequence of SEQ ID NO: 4 are shown in FIG. 2.

Example 1

Introduction of T103E Mutation into K3-1115 Gene (Production of Expression Construct)

Since Siglec-15 is a basic protein, the binding affinity is expected to be improved with a new ionic bond between the antigen and the antibody, which is obtained by introducing an acidic amino acid residue such as aspartic acid or glutamic acid into the antibody sequence. A substitution variant was designed in which a glutamic acid residue, which is an acidic amino acid and has a long side chain, was introduced into the antibody at the position of a threonine residue, which is located in the center of the CDRH3 loop, which is considered to be the most important CDR at the antibody recognition site and is presumed to face the antigen based on an X-ray crystal structure analysis. As the heavy chain sequence into which the substitution is to be introduced, the K3-1115 heavy chain was selected, and the heavy chain sequence in which a threonine residue, which is the amino acid residue at position 3 in the CDRH3 sequence of the K3-1115 heavy chain sequence, was substituted with a glutamic acid residue was named "K3-1115/T103E heavy chain". The substitution position of the amino acid residue corresponds to position 103 in the K3-1115 heavy chain sequence from which the signal sequence has been removed. Incidentally, the "K3-1115/T103E heavy chain" is sometimes referred to as "K3-1115/1103E antibody heavy chain".

By using pEG2/h#32A1-H1-1 as described in Example 28 in WO 2010/117011 as a template, and also using, for example, QuikChange Lightning Site-Directed Mutagenesis Kit (Agilent Technologies, Inc.) and the following primer set, base substitution is performed according to the protocol attached to the kit, whereby a K3-1115/T103E heavy chain expression vector can be constructed. The obtained expression vector was named "pEG2/K3-1115/T103E".

Primer Set for Introduction of Base Substitution

```
5'-CTACTACTGCGCCAGGTCCTTGGAGGGCGGCGAC-3'
(32A1_HT103EFw: SEQ ID NO: 15 in Sequence Listing)

5'-GTCGCCGCCCTCCAAGGACCTGGCGCAGTAGTAG-3'
(32A1_HT103ERv: SEQ ID NO: 16 in Sequence Listing)
```

The amino acid sequence of the K3-1115/T103E heavy chain is represented by SEQ ID NO: 6 in the Sequence Listing. The sequence comprising amino acid residues 1 to 19 of the amino acid sequence of SEQ ID NO: 6, the sequence comprising amino acid residues 20 to 140 thereof, and the sequence comprising amino acid residues 141 to 466 thereof, correspond to the signal sequence, the heavy chain variable region, and the heavy chain constant region, respectively. A nucleotide sequence encoding the amino acid sequence of SEQ ID NO: 6 is represented by SEQ ID NO: 5 in the Sequence Listing. The sequence comprising nucleotides 1 to 57 of the nucleotide sequence of SEQ ID NO: 5, the sequence comprising nucleotides 58 to 420 thereof, and the sequence comprising nucleotides 421 to 1398 thereof, encode the signal sequence, the heavy chain variable region sequence, and the heavy chain constant region sequence, respectively. The nucleotide sequence of SEQ ID NO: 5 and the amino acid sequence of SEQ ID NO: 6 are shown in FIG. 3.

Example 2

Preparation of K3-1115 Antibody and K3-1115/T103E Antibody 2-1) Production of K3-1115 Antibody and K3-1115/T103E Antibody The antibodies were produced according to the following method or a modified method thereof. FreeStyle 293F cells (Invitrogen Corporation) were subcultured and cultured according to the protocol. $1.2 \times 10^9$ cells of FreeStyle 293F cells (Invitrogen Corporation) in logarithmic growth phase were seeded in a 3-L Fernbach Erlenmeyer Flask (Corning Incorporated) and prepared at $1.0 \times 10^6$ cells/ml by dilution with FreeStyle 293 expression medium (Invitrogen Corporation), and then, shaking culture was performed at 90 rpm for 1 hour at 37° C. in an 8% $CO_2$ incubator. 3.6 mg of polyethyleneimine (Polyscience #24765) was dissolved in 20 ml of Opti-Pro SFM medium (Invitrogen Corporation). Subsequently, a heavy chain expression vector (0.4 mg) and a light chain expression vector (0.8 mg) prepared using NucleoBond Xtra (TaKaRa Bio, Inc.) were suspended in 20 ml of Opti-Pro SFM medium (Invitrogen Corporation). Then, 20 ml of the obtained expression vectors/Opti-Pro SFM mixture was added to 20 ml of the obtained polyethyleneimine/Opti-Pro SFM mixture, and the resulting mixture was gently stirred and then left for 5 minutes. Thereafter, the mixture was added to the FreeStyle 293F cells, and shaking culture was performed at 90 rpm for 7 days at 37° C. in an 8% $CO_2$ incubator. The resulting culture supernatant was filtered through a disposable capsule filter (Advantec #CCS-045-E1H).

In the above culture, by combining the heavy chain expression vector pEG2/h#32A1-H1-1 and the light chain expression vector pEF6KCL/h#32A1-L2-15 described in WO 2010/117011, the K3-1115 antibody can be produced.

Further, by combining the heavy chain expression vector pEG2/K3-1115/T103E produced in Example 1 and the light chain expression vector pEF6KCL/h#32A1-L2-15 described in WO 2010/117011, a one-amino acid residue substitution variant of the humanized antibody of the rat anti-mouse Siglec-15 monoclonal antibody #32A1 can be produced. The one-amino acid residue substitution variant was named "K3-1115/T103E". In this specification, the "K3-1115/T103E" is sometimes referred to as "K3-1115/T103E antibody". As described in the above preparation method of the antibody, the light chain sequence of the K3-1115 antibody and the K3-1115/T103E antibody is the same. That is, between the K3-1115 antibody and the K3-1115/T103E antibody, only one amino acid residue in the CDRH3 of the heavy chain is different.

2-2) Purification of K3-1115 and K3-1115/T103E Antibodies

The K3-1115 and K3-1115/T103E antibodies were purified according to the following method or a modified method thereof.

The culture supernatant obtained in the above 2-1) was subjected to purification by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe (manufactured by GE Healthcare Bio-Sciences Ltd., 2×1 ml HiTrap columns in series) equilibrated with PBS. After all of the culture solution was poured into the column, the column was washed with 15 to 30 ml of PBS. Subsequently, elution was performed with a 2 M arginine hydrochloride solution (pH 4.0), and a fraction containing the antibody was collected. The collected fraction was subjected to buffer replacement with a buffer containing 5 mM sodium phosphate, 50 mM MES, and 20 mM NaCl at pH 6.5 using a desalting column (manufactured by GE Healthcare Bio-Sciences Ltd., 2×5 ml HiTrap desalting columns in series). Further, the antibody solution subjected to buffer replacement was applied to a ceramic hydroxyapatite column (Bio-Rad Laboratories, Inc. (Japan), Bio-Scale CHT2-1 hydroxyapatite column (2 ml volume)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The collected fraction was subjected to liquid replacement with CBS (10 mM citrate buffer containing 140 mM sodium chloride, pH 6.0) using a desalting column (manufactured by GE Healthcare Bio-Sciences Ltd., 2×5 ml HiTrap desalting columns in series). Finally, the resulting solution was concentrated using Centrifugal UF Filter Device VIVASPIN 20 (fractional molecular weight: 30 K, Sartorius Co., Ltd., at 4° C.), the concentration of IgG was adjusted to 1.0 mg/ml or more, and the thus obtained solution was used as a purified sample.

Example 3

Evaluation of Binding Activity of K3-1115/T103E Antibody to Human Siglec-15 Protein 3-1) Expression and Purification of Human Siglec-15 V-Set Domain A DNA encoding a protein in which a His tag and a Factor Xa recognition sequence were attached to the N-terminal side of a human Siglec-15 V-set domain (a polypeptide comprising amino acid residues 39 to 165 of an amino acid sequence with the accession number of NP 998767 in the NCBI Protein database) was integrated into a vector pDEST14 (Invitrogen, Corporation, Cat. No. 11801-016). By using this plasmid, *Escherichia coli* Rosetta-gamiB (DE3) (Novagen, Inc., Cat. No. 71136-4) was transformed and cultured in TB medium (Invitrogen, Corporation, Cat. No. 22711-022). After culturing, the bacterial cells were homogenized by ultrasound, the resulting homogenate was centrifuged, and the supernatant was subjected to purification using a HisTrap HP column (GE Healthcare Ltd., Cat. No. 17-5247-01). Thereafter, the His tag was cleaved with Factor Xa (New England BioLabs Inc., Cat. No. P8010L), and then the human Siglec-15 V-set domain was purified using a Mono S5/50 GL column (GE Healthcare Ltd., Cat. No. 17-5168-01) and a Superdex 75 10/300 column (GE Healthcare Ltd., Cat. No. 17-5174-01) until a single band with a molecular weight of 14 kDa was obtained by electrophoresis.

3-2) Measurement of Dissociation Constant Between K3-1115 or K3-1115/T103E and Human Siglec-15 V-Set Domain The dissociation constant between the K3-1115 or K3-1115/T103E antibody and the hSiglec-15 (39-165) V-set domain was measured using Biacore T200 (GE Healthcare Bio-Sciences Ltd.) by immobilizing the antibody as a ligand and using the antigen as an analyte. The K3-1115 or K3-1115/T103E antibody was bound to the sensor chip CM5 (GE Healthcare Bio-Sciences Ltd.) at about 50 RU by an amine coupling method via an anti-human IgG antibody (GE Healthcare Bio-Sciences Ltd.) immobilized thereon. As a running buffer, HBS-EP+ (10 mM HEPES pH 7.4, 0.15 M NaCl, 3 mM EDTA, 0.05% surfactant P20) was used. On the chip having the antibody bound thereto, a dilution series of an antigen solution (0.003 to 7 nM) was added at a flow rate of 90 μL/min for 233 seconds, and subsequently, the dissociation phase was monitored for 2000 to 3600 seconds. As a regeneration solution, 3 M $MgCl_2$ was added at a flow rate of 10 μL/min for 30 seconds. In the analysis of data, a 1:1 binding model of analysis software (Biacore T200 Evaluation software, version 1.0) was used, and an association rate constant (kon), a dissociation rate constant (koff), and a dissociation constant (KD; KD=koff/kon) were calculated. As a result, K3-1115 had a KD value of 2.6E-10 [M], and K3-1115/T103E had a KD value of 4.1E-12 [M], and it was revealed that by the substitution of one amino acid residue, the affinity of K3-1115/T103E was about 60 times more enhanced compared with that of K3-1115. Incidentally, as the one-amino acid substitution variant of K3-1115, 121 types of antibodies were produced according to the method described in Example 2 or a modified method thereof, and evaluated for binding activity to the human Siglec-15 protein according to the method described in Example 3 or a modified method thereof. Among these 121 types of substitution variants, there were 6 types of antibodies showing higher affinity for the human Siglec-15 protein than K3-1115, and K3-1115/T103E showed the highest affinity among these antibodies.

Example 4

Effect of K3-1115/T103E Antibody on Mouse Osteoclast Formation

The femur and tibia are excised from a male ddY mouse at the age of 5 to 8 weeks and soft tissues are removed. Both ends of the femur or tibia are cut off, and D-PBS is injected using a syringe with a 25-gauge injection needle to push out bone marrow cells, which are collected in a centrifugal tube. Centrifugation is performed at room temperature for 5 minutes at 100 g, and the supernatant is removed. To the resulting cell pellet, 1 ml of a hemolytic buffer (Red Blood Cell Lysing Buffer, manufactured by Sigma Co., Ltd.) is added to suspend the pellet, and the resulting suspension is left at room temperature for 5 minutes. 20 ml of D-PBS is added thereto, and the suspension is centrifuged at room temperature for 5 minutes at 100 g, and the supernatant is removed. To the resulting cell pellet, 10 ml of MEM-α medium (manufactured by Invitrogen, Corporation) containing 5 ng/ml of M-CSF (manufactured by R&D Systems, Inc.) and 10% fetal bovine serum (FBS) is added to suspend the pellet. Then, the resulting suspension is passed through a cell strainer (40 μm Nylon, manufactured by BD Falcon) to remove aggregates. The resulting cells are transferred to a 75 cm² T-flask (for the attachment of adherent cells) and cultured overnight in a $CO_2$ incubator. After the overnight culture, the cells which do not adhere to the T-flask are recovered and used as mouse bone marrow nonadherent cells. The mouse bone marrow nonadherent cells prepared by the method described above are prepared at $1.5 \times 10^5$ cells/ml in α-MEM medium containing 10% FBS and 10 ng/ml of M-CSF (manufactured by R&D Systems, Inc.), and the resulting cell preparation is seeded in each well of a 96-well plate in an amount of 200 μl and the cells are cultured for 2 days in a $CO_2$ incubator. The old culture solution in the 96-well plate is removed, and 100 μl of MEM-α medium is added to each well, the 100 μl of MEM-α medium containing 10% FBS to which human RANKL (RANKL, manufactured by Peprotech, Inc.) and M-CSF have been added to give final concentrations of 20 ng/ml and 10 ng/ml, respectively. To the cell culture solution, the K3-1115/T103E antibody prepared in Example 2 is added at a concentration of 3 to 100 ng/ml, and the cells are cultured for additional 3 days in a $CO_2$ incubator. After completion of the culturing, the activity of tartrate-resistant acid phosphatase (TRAP) of the formed osteoclasts is measured by a procedure described below. The culture solution in each well of the 96-well plate is removed by suction, and 50 μl of 50 mM sodium citrate buffer (pH 6.1) containing 1% Triton X-100 is added to each well. Then, the plate is shaken for 5 minutes on a plate shaker to lyse the cells. To each well, 50 μl of a substrate solution (50 mM sodium citrate buffer (pH 6.1) containing 5 mg/ml p-nitrophenyl phosphate and 0.46% sodium tartrate) is added, and the plate is incubated at room temperature for 10 minutes. After the incubation, 50 μl of a 1 N sodium hydroxide solution is added to each well of the 96-well plate to stop the enzymatic reaction. After stopping the enzymatic reaction, an absorbance of each well at 405 nm is measured, and the obtained absorbance is used as an index of TRAP activity. By comparison of the TRAP activity with the case where the antibody is not added, the inhibitory effect of the K3-1115/T103E antibody on the mouse osteoclast formation can be evaluated.

Example 5

Effect of K3-1115/T103E Antibody on Bone Resorption Activity of Normal Human Osteoclasts (In Vitro Evaluation of Biological Activity)

It is known that osteoclasts release a protease such as cathepsin K and degrade type I collagen which is a constitutional component of bone tissue. OsteoLyse Assay Kit (manufactured by Lonza, Inc., Cat. No. PA-1500) provides a 96-well plate coated with europium-conjugated human collagen (96-well OsteoLyse cell culture plate), and it is possible to evaluate the bone resorption activity of osteoclasts in vitro by measuring the amount of fluorescent collagen fragments released in the supernatant when osteoclasts are cultured in the plate.

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate at $1 \times 10^4$ cells/well according to the protocol attached to the cells. Incidentally, as the medium, a basal medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 63.8 ng/ml), human M-CSF (final concentration: 33 ng/ml), and the like was used. To this culture supernatant, each of the K3-1115 antibody and the K3-1115/T103E antibody prepared in Example 2 were added to give a final concentration of 0.8, 4, 20, or 100 ng/ml, and the cells were cultured for 5 days in a $CO_2$ incubator. A 10-μL aliquot of the culture supernatant was collected, and 200 μL of Fluorophore Releasing Reagent included in the OsteoLyse Assay Kit was added thereto, and a fluorescence intensity was measured (Excitation: 340 nm, Emission: 615 nm) using a fluorescence plate reader (ARVO MX, manufactured by Perkin Elmer Inc.), whereby the amount of free fluorescent collagen fragments released in the culture supernatant was determined (FIG. 5). As a result, the amount of free collagen fragments was reduced by the K3-1115 antibody in a concentration-dependent manner within the range from 20 ng/ml to 100 ng/ml. On the other hand, by the addition of the K3-1115/T103E antibody, the amount of free collagen fragments was reduced in a concentration-dependent manner within the range from 4 ng/ml to 100 ng/ml. From this result, it was revealed that the K3-1115/T103E antibody strongly inhibits the bone resorption activity of human osteoclasts at a lower concentration than the K3-1115 antibody.

Example 6

Biological Evaluation of K3-1115/T103E Antibody Using Ovariectomized Rats a) Protocol of Animal Experiment The ovaries on both sides are removed from female F344 rats at the age of 12 weeks (obtained from Charles River Laboratories Japan, Inc.), and the rats are divided into two groups: a vehicle administration group; and a K3-1115/T103E antibody administration group. Further, one group is also prepared as a sham operation group. In the antibody administration group, the K3-1115/T103E antibody prepared in Example 2 is intraperitoneally administered at a dose of 1 mg/kg three times a week repeatedly for 4 weeks from the next day of the operation. In the vehicle administration group and the sham operation group, PBS containing 0.01% Tween 20 is intraperitoneally administered as the vehicle. After 4 weeks from the initiation of administration, urine is collected for 24 hours under fasting conditions, and the urine samples are stored at $-80°$ C. until measurement. After completion of the urine collection, the rats are euthanized, and the lumbar spine is excised from each rat.

b) Measurement of Lumbar Spine Bone Mineral Density

Soft tissues adhered to the excised lumbar spine are removed, and the 4th to 6th lumbar vertebrae are extracted. The extracted lumbar vertebrae are degreased and dehydrated by being shaken in ethanol and then air-dried, and the bone mineral density is measured using a bone densitometer (DCS-600EX, manufactured by Aloka Co., Ltd.). A significant decrease in lumbar spine bone mineral density is observed in the ovariectomized group as compared with the sham operation group, however, in the K3-1115/T103E antibody administration group, a decrease in bone mineral density due to ovariectomy is significantly inhibited. By adding one group in which K3-1115 is administered to the protocol described in a), the inhibitory effect on the bone mineral density phenomenon can be compared between K3-1115 and K3-1115/T103E.

c) Measurement of Urinary Deoxypyridinoline Excretion

A variety of type I collagen crosslinked metabolites sharply reflect bone metabolic turnover, particularly bone resorption. Above all, deoxypyridinoline is localized mainly in bone collagen, and therefore it is considered to be highly reliable as an index of bone resorption.

The cryopreserved urine sample is thawed, and insoluble matter is precipitated by a centrifugal operation, whereby a supernatant is obtained. The amount of deoxypyridinoline contained in this supernatant is measured using Osteolinks "DPD" (manufactured by DS Pharma Biomedical Co., Ltd.). Further, by using Creatinine Test Wako (manufactured by Wako Pure Chemical Industries, Ltd.), the content of creatinine in the supernatant is also measured, and the amount of deoxypyridinoline corrected for creatinine is calculated. The urinary deoxypyridinoline excretion is significantly increased in the ovariectomized group as compared with the sham operation group, and therefore, it is indicated that in the ovariectomized rats, osteoclastic bone resorption is increased. On the other hand, in the K3-1115/T103E antibody administration group, an increase in deoxypyridinoline excretion due to ovariectomy is inhibited such that the level of deoxypyridinoline excretion is comparable to that of the sham operation group. From this result, it is also confirmed in the animal model that the studied monoclonal antibody specifically binding to Siglec-15 inhibits osteoclastic bone resorption, and it is strongly suggested that due to the inhibitory effect on bone resorption, a decrease in lumbar spine bone mineral density in the ovariectomized rats is inhibited. By adding one group in which K3-1115 is administered to the protocol described in a), the inhibitory effect on the bone mineral density phenomenon can be compared between K3-1115 and K3-1115/T103E.

Example 7

Biological Evaluation of K3-1115/T103E Antibody Using Ovariectomized Monkeys

The inhibitory effect of the K3-1115/T103E antibody on bone resorption activity in ovariectomized monkeys can be evaluated by the method described below.

The ovaries on both sides are removed from female cynomolgus monkeys at the age of 7 to 15 years, and after one month the monkeys are divided into a vehicle administration group and a K3-1115/T103E antibody administration group. In the antibody administration group, the K3-1115/T103E antibody prepared in Example 2 is subcutaneously administered at a single dose of 0.1 to 30 mg/kg. Urine and blood are collected over time until about two months after the administration. By measuring a bone metabolism marker in the urine and blood, the activity of inhibiting the bone resorption of the antibody is evaluated. Examples of the bone metabolism marker include bone resorption markers such as urinary N-telopeptide of type I collagen (NTX), urinary C-telopeptide of type I collagen (CTX), blood NTX, blood CTX, and blood tartrate-resistant acid phosphatase (TRAP5b), and bone formation markers such as blood bone alkaline phosphatase (BAP), blood osteocalcin (BGP), and procollagen type I C-peptide (P1NP).

INDUSTRIAL APPLICABILITY

The CDR-modified variant of the humanized anti-Siglec-15 antibody of the invention has a higher ability to inhibit osteoclast differentiation or bone resorption activity than known antibodies, and a pharmaceutical composition containing the anti-Siglec-15 antibody can be a therapeutic or prophylactic agent for a disease of abnormal bone metabolism.

SEQUENCE LISTING FREE TEXT

SEQ ID NO: 1: nucleotide sequence of K3-1115 antibody heavy chain
SEQ ID NO: 2: amino acid sequence of K3-1115 antibody heavy chain
SEQ ID NO: 3: nucleotide sequence of K3-1115 antibody light chain
SEQ ID NO: 4: amino acid sequence of K3-1115 antibody light chain
SEQ ID NO: 5: nucleotide sequence of K3-1115/T103E antibody heavy chain
SEQ ID NO: 6: amino acid sequence of K3-1115/T103E antibody heavy chain
SEQ ID NO: 7: amino acid sequence of CDRH1 of #32A1 antibody
SEQ ID NO: 8: amino acid sequence (comprising 19 amino acid residues) of CDRH2 of #32A1 antibody
SEQ ID NO: 9: amino acid sequence (comprising 14 amino acid residues) of CDRH2 of #32A1 antibody
SEQ ID NO: 10: amino acid sequence of CDRH3 of #32A1 antibody
SEQ ID NO: 11: amino acid sequence of CDRH3 of K3-1115/T103E antibody
SEQ ID NO: 12: amino acid sequence of CDRL1 of #32A1 antibody
SEQ ID NO: 13: amino acid sequence of CDRL2 of #32A1 antibody
SEQ ID NO: 14: amino acid sequence of CDRL3 of #32A1 antibody
SEQ ID NO: 15: PCR primer 32A1_HT103EFw
SEQ ID NO: 16: PCR primer 32A1_HT103ERv

The invention claimed is:

1. An antibody or an antigen binding fragment, comprising:
   a heavy chain sequence that comprises a variable region having CDRH1, CDRH2, and CDRH3, wherein CDRH1 comprises SEQ ID NO: 7, CDRH2 comprises SEQ ID NO: 9, and CDRH3 comprises SEQ ID NO: 11; and
   a light chain sequence that comprises a variable region having CDRL1, CDRL2, and CDRL3, wherein CDRL1 comprises SEQ ID NO: 12, CDRL2 comprises SEQ ID NO: 13, and CDRL3 comprises SEQ ID NO: 14,
   wherein the antibody or antigen binding fragment binds Siglec-15.

2. The antibody or an antigen binding fragment according to claim 1, comprising a heavy chain variable region sequence that comprises amino acid residues 20 to 140 of SEQ ID NO: 6 and a light chain variable region sequence that comprises amino acid residues 21 to 133 of SEQ ID NO: 4.

3. The antibody or an antigen binding fragment according to claim 1, comprising a heavy chain sequence that comprises amino acid residues 20 to 466 of SEQ ID NO: 6 and a light chain sequence that comprises amino acid residues 21 to 238 of SEQ ID NO: 4.

4. The antibody or an antigen binding fragment according to claim 1, comprising a heavy chain sequence that comprises amino acid residues 20 to 465 of SEQ ID NO: 6 and a light chain sequence that comprises amino acid residues 21 to 238 of SEQ ID NO: 4.

5. The antigen binding fragment according to claim 1, which is selected from the group consisting of Fab, F(ab')2, Fab' and Fv.

6. The antibody according to claim 1, wherein the antibody is an scFv.

7. A pharmaceutical composition, characterized by comprising at least one antibody or antigen binding fragment according to claim 1, wherein said antibody or antigen binding fragment inhibits osteoclast formation and/or osteoclastic bone resorption.

8. The pharmaceutical composition according to claim 7, wherein the composition is a therapeutic and/or prophylactic agent for abnormal bone metabolism, wherein said abnormal bone metabolism is characterized by insufficient bone mass or density.

9. A pharmaceutical composition for the treatment and/or prophylaxis of abnormal bone metabolism, comprising at least one antibody or antigen binding fragment according to claim 1, wherein said antibody or antigen binding fragment inhibits osteoclast formation and/or osteoclastic bone resorption, and wherein said abnormal bone metabolism is characterized by insufficient bone mass or density, and at least one therapeutic agent selected from the group consisting of bisphosphonates, active vitamin $D_3$, calcitonin and derivatives thereof, hormones, estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or antigen binding fragments of the antibodies, anti-PTHrP (parathyroid hormone-related protein) antibodies or antigen binding fragments of the antibodies, IL-1 receptor antagonists, anti-IL-6 receptor antibodies or antigen binding fragments of the antibodies, anti-RANKL antibodies or antigen binding fragments of the antibodies, and OCIF (osteoclastogenesis inhibitory factor).

10. The pharmaceutical composition according to claim 8, wherein the abnormal bone metabolism is selected from the group consisting of osteoporosis, bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, bone Paget's disease, renal osteodystrophy, and osteogenesis imperfecta.

11. The pharmaceutical composition according to claim 10, wherein the abnormal bone metabolism is osteoporosis, bone destruction accompanying rheumatoid arthritis, or bone destruction accompanying cancer metastasis to bone.

12. The pharmaceutical composition according to claim 11, characterized in that the abnormal bone metabolism is osteoporosis.

13. The pharmaceutical composition according to claim 12, wherein the osteoporosis is postmenopausal osteoporosis, senile osteoporosis, secondary osteoporosis due to the use of a therapeutic agent, or osteoporosis accompanying rheumatoid arthritis.

14. A method for the treatment and/or prophylaxis of abnormal bone metabolism, wherein said abnormal bone metabolism is characterized by insufficient bone mass or density, comprising administering to a human at least one antibody or antigen binding fragment according to claim 1, wherein said antibody or antigen binding fragment inhibits osteoclast formation and/or osteoclastic bone resorption.

15. A method for the treatment and/or prophylaxis of abnormal bone metabolism, comprising simultaneously or successively administering to a human at least one antibody or antigen binding fragment according claim 1, wherein said antibody or antigen binding fragment inhibits osteoclast formation and/or osteoclastic bone resorption, and wherein said abnormal bone metabolism is characterized by insufficient bone mass or density, and at least one therapeutic agent selected from the group consisting of bisphosphonates, active vitamin $D_3$, calcitonin and derivatives thereof, hormones, estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or antigen binding fragments of the antibodies, anti-PTHrP (parathyroid hormone-related protein) antibodies or antigen binding fragments of the antibodies, IL-1 receptor antagonists, anti-IL-6 receptor antibodies or antigen binding fragments of the antibodies, anti-RANKL antibodies or antigen binding fragments of the antibodies, and OCIF (osteoclastogenesis inhibitory factor).

16. The method for the treatment and/or prophylaxis according to claim 14, wherein the abnormal bone metabolism is osteoporosis, bone destruction accompanying rheumatoid arthritis, or bone destruction accompanying cancer metastasis to bone.

17. The method for the treatment and/or prophylaxis according to claim 16, wherein the abnormal bone metabolism is osteoporosis.

18. The method for the treatment and/or prophylaxis according to claim 17, wherein the osteoporosis is postmenopausal osteoporosis, senile osteoporosis, secondary osteoporosis due to the use of a therapeutic agent, or osteoporosis accompanying rheumatoid arthritis.

19. A polynucleotide encoding the antibody according to claim 1.

20. The polynucleotide according to claim 19, comprising a nucleotide sequence that comprises nucleotides 58 to 420 of SEQ ID NO: 5 and a nucleotide sequence that comprises nucleotides 61 to 399 of SEQ ID NO: 3.

21. The polynucleotide according to claim 19, comprising a nucleotide sequence that comprises nucleotides 58 to 1398 of SEQ ID NO: 5 and a nucleotide sequence that comprises nucleotides 61 to 714 of SEQ ID NO: 3.

22. A vector, comprising a polynucleotide according to claim 19.

23. A transformed host cell, comprising a polynucleotide according to claim 19.

24. A transformed host cell, comprising the vector according to claim 22.

25. A method of producing an antibody, comprising culturing the host cell according to claim 23, and purifying an antibody from the resulting culture product.

26. The antibody or antigen binding fragment according to claim 1, wherein the heavy chain includes a deletion of one or two amino acids from the carboxyl terminus.

27. The antibody or antigen binding fragment according to claim 1, wherein glycosylation is controlled to enhance an antibody-dependent cytotoxic activity.

28. An immunoconjugate comprising the antibody according to claim 1 and a compound having a pharmacological effect.

* * * * *

SEQUENCE LISTING

```
<160> NUMBER OF SEQ ID NOS: 16

<210> SEQ ID NO 1
<211> LENGTH: 1398
<212> TYPE: DNA
<213> ORGANISM: Artificial Sequence
<220> FEATURE:
<223> OTHER INFORMATION: Heavy chain of K3-1115
<220> FEATURE:
<221> NAME/KEY: CDS
```

<222> LOCATION: (1)..(1398)

<400> SEQUENCE: 1

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtc cag ctt gtg gaa agc gga ggg gga ctc gtt cag      96
Val Leu Ser Glu Val Gln Leu Val Glu Ser Gly Gly Gly Leu Val Gln
            20                  25                  30 cca gga ggc tct ctg cgc ctg tca tgc gct gcc agc gga ttt aat ttc     144
Pro Gly Gly Ser Leu Arg Leu Ser Cys Ala Ala Ser Gly Phe Asn Phe
        35                  40                  45 aat gat tat ttt atg aac tgg gtc agg cag gct ccg gga aaa ggg ctg     192
Asn Asp Tyr Phe Met Asn Trp Val Arg Gln Ala Pro Gly Lys Gly Leu
    50                  55                  60 gaa tgg gtc gcc cag atc aga aac aag atc tat act tac gct aca ttc     240
Glu Trp Val Ala Gln Ile Arg Asn Lys Ile Tyr Thr Tyr Ala Thr Phe
65                  70                  75                  80 tac gcc gca tct gta aag ggg agg ttt aca att agt cgc gac aat gca     288
Tyr Ala Ala Ser Val Lys Gly Arg Phe Thr Ile Ser Arg Asp Asn Ala
                85                  90                  95 aaa aat agt ctg tat ctc caa atg aac tcc ctc cgc gca gag gat act     336
Lys Asn Ser Leu Tyr Leu Gln Met Asn Ser Leu Arg Ala Glu Asp Thr
            100                 105                 110 gct gtc tac tac tgc gcc agg tcc ttg act ggc ggc gac tat ttt gat     384
Ala Val Tyr Tyr Cys Ala Arg Ser Leu Thr Gly Gly Asp Tyr Phe Asp
        115                 120                 125 tac tgg gga cag ggc acc ctg gtg acg gtg agc tca gcc agc acc aag     432
Tyr Trp Gly Gln Gly Thr Leu Val Thr Val Ser Ser Ala Ser Thr Lys
    130                 135                 140 ggc cct tcc gtg ttc cct ctg gcc cct tgt agc cgt tcc acc agc gag     480
Gly Pro Ser Val Phe Pro Leu Ala Pro Cys Ser Arg Ser Thr Ser Glu
145                 150                 155                 160 tcc acc gcc gcc ctt ggc tgt ctg gtg aag gac tac ttc cct gag cct     528
Ser Thr Ala Ala Leu Gly Cys Leu Val Lys Asp Tyr Phe Pro Glu Pro
                165                 170                 175 gtg acc gtg agc tgg aac tcc gga gcc ctt acc agc ggc gtg cac acc     576
Val Thr Val Ser Trp Asn Ser Gly Ala Leu Thr Ser Gly Val His Thr
            180                 185                 190 ttc cct gcc gtg ctg cag tcc agc ggc ctt tac tcc ctg agc tcc gtg     624
Phe Pro Ala Val Leu Gln Ser Ser Gly Leu Tyr Ser Leu Ser Ser Val
        195                 200                 205 gtg acc gtg cct agc tcc aac ttc ggc acc caa acc tac acc tgt aac     672
Val Thr Val Pro Ser Ser Asn Phe Gly Thr Gln Thr Tyr Thr Cys Asn
    210                 215                 220 gtg gac cac aag cct agc aac acc aag gtg gac aag acc gtg gag cgt     720
Val Asp His Lys Pro Ser Asn Thr Lys Val Asp Lys Thr Val Glu Arg
225                 230                 235                 240 aag tgt tgt gtg gag tgt cct cct tgt cct gcc cct cct gtg gcc gga     768
Lys Cys Cys Val Glu Cys Pro Pro Cys Pro Ala Pro Pro Val Ala Gly
                245                 250                 255 cct tcc gtg ttc ctt ttc cct cct aag cct aag gac acc ctg atg atc     816
Pro Ser Val Phe Leu Phe Pro Pro Lys Pro Lys Asp Thr Leu Met Ile
            260                 265                 270 agc cgt acc cct gag gtg acc tgt gtg gtg gtg gac gtg tcc cac gag     864
Ser Arg Thr Pro Glu Val Thr Cys Val Val Val Asp Val Ser His Glu
        275                 280                 285 gac cct gag gtg cag ttc aac tgg tac gtg gac ggc gtg gag gtg cac     912
Asp Pro Glu Val Gln Phe Asn Trp Tyr Val Asp Gly Val Glu Val His
    290                 295                 300
```

-continued

```
aac gcc aag acc aag cct cgt gag gag caa ttc aac agc acc ttc cgt      960
Asn Ala Lys Thr Lys Pro Arg Glu Glu Gln Phe Asn Ser Thr Phe Arg
305             310                 315                 320 gtg gtg tcc gtg ctt acc gtg gtg cac caa gac tgg ctg aac ggc aag     1008
Val Val Ser Val Leu Thr Val Val His Gln Asp Trp Leu Asn Gly Lys
                325                 330                 335 gag tac aag tgt aag gtg agc aac aag gga ctt cct gcc cct atc gag     1056
Glu Tyr Lys Cys Lys Val Ser Asn Lys Gly Leu Pro Ala Pro Ile Glu
            340                 345                 350 aag acc atc tcc aag acc aag ggc caa cct cgt gag cct caa gtg tac     1104
Lys Thr Ile Ser Lys Thr Lys Gly Gln Pro Arg Glu Pro Gln Val Tyr
        355                 360                 365 acc ctt cct cct agc cgt gag gag atg acc aag aac caa gtg tcc ctt     1152
Thr Leu Pro Pro Ser Arg Glu Glu Met Thr Lys Asn Gln Val Ser Leu
    370                 375                 380 acc tgt ctg gtg aag ggc ttc tac cct agc gac atc gcc gtg gag tgg     1200
Thr Cys Leu Val Lys Gly Phe Tyr Pro Ser Asp Ile Ala Val Glu Trp
385                 390                 395                 400 gag tcc aac gga caa cct gag aac aac tac aag acc acc cct cct atg     1248
Glu Ser Asn Gly Gln Pro Glu Asn Asn Tyr Lys Thr Thr Pro Pro Met
                405                 410                 415 ctt gac agc gac ggc tcc ttc ttc ctg tac agc aag ctg acc gtg gac     1296
Leu Asp Ser Asp Gly Ser Phe Phe Leu Tyr Ser Lys Leu Thr Val Asp
            420                 425                 430 aag tcc cgt tgg caa caa ggc aac gtg ttc agc tgt tcc gtg atg cac     1344
Lys Ser Arg Trp Gln Gln Gly Asn Val Phe Ser Cys Ser Val Met His
        435                 440                 445 gag gcc ctg cac aac cac tac acc caa aag agc ctt tcc ctg agc cct     1392
Glu Ala Leu His Asn His Tyr Thr Gln Lys Ser Leu Ser Leu Ser Pro
    450                 455                 460 gga aag                                                             1398
Gly Lys
465

<210> SEQ ID NO 2
<211> LENGTH: 466
<212> TYPE: PRT
<213> ORGANISM: Artificial Sequence
<220> FEATURE:
<223> OTHER INFORMATION: Synthetic Construct

<400> SEQUENCE: 2

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys Ile Tyr Thr Tyr Ala Thr Phe
65                  70                  75                  80

Tyr Ala Ala Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Ser Leu Thr Gly Gly Asp Tyr Phe Asp
        115                 120                 125
```

Tyr Trp Gly Gln Gly Thr Leu Val Thr Val Ser Ser Ala Ser Thr Lys
        130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Asp Val Ser His Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 3
<211> LENGTH: 714
<212> TYPE: DNA
<213> ORGANISM: Artificial Sequence
<220> FEATURE:
<223> OTHER INFORMATION: Light chain of K3-1115
<220> FEATURE:
<221> NAME/KEY: CDS
<222> LOCATION: (1)..(714)

<400> SEQUENCE: 3

```
atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gca tat ggc gaa att ctg atg acg cag agt cct gca act ctt agt    96
Gly Ala Tyr Gly Glu Ile Leu Met Thr Gln Ser Pro Ala Thr Leu Ser
                20                  25                  30 ctg tca cct ggc gag aga gcc aca ctc agc tgc cga gcg tcc cag tcc   144
Leu Ser Pro Gly Glu Arg Ala Thr Leu Ser Cys Arg Ala Ser Gln Ser
            35                  40                  45 gtg acc att agc ggc tat tct ttt att cat tgg tat cag caa aag cct   192
Val Thr Ile Ser Gly Tyr Ser Phe Ile His Trp Tyr Gln Gln Lys Pro
        50                  55                  60 gga cag gcg cca agg ctg ctc att tac aga gca agc aac ctt gcc tct   240
Gly Gln Ala Pro Arg Leu Leu Ile Tyr Arg Ala Ser Asn Leu Ala Ser
65              70                  75                  80 ggc att cca gca aga ttc agc ggg agc gga tca ggg aca gat ttc acc   288
Gly Ile Pro Ala Arg Phe Ser Gly Ser Gly Ser Gly Thr Asp Phe Thr
                85                  90                  95 ttg acc atc tcc tcc ctg gag ccg gag gat ttc gcg ttg tat tat tgt   336
Leu Thr Ile Ser Ser Leu Glu Pro Glu Asp Phe Ala Leu Tyr Tyr Cys
                100                 105                 110 cag caa tct agg aag agt cca tgg aca ttt ggc cag ggc acc aaa gtg   384
Gln Gln Ser Arg Lys Ser Pro Trp Thr Phe Gly Gln Gly Thr Lys Val
            115                 120                 125 gag atc aag cgt acg gtg gcc gcc ccc tcc gtg ttc atc ttc ccc ccc   432
Glu Ile Lys Arg Thr Val Ala Ala Pro Ser Val Phe Ile Phe Pro Pro
130                 135                 140 tcc gac gag cag ctg aag tcc ggc acc gcc tcc gtg gtg tgc ctg ctg   480
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac   528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc   576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc   624
Lys Asp Ser Thr Tyr Ser Leu Ser Ser Thr Leu Thr Leu Ser Lys Ala
        195                 200                 205 gac tac gag aag cac aag gtg tac gcc tgc gag gtg acc cac cag ggc   672
Asp Tyr Glu Lys His Lys Val Tyr Ala Cys Glu Val Thr His Gln Gly
    210                 215                 220 ctg agc tcc ccc gtc acc aag agc ttc aac agg ggg gag tgt             714
Leu Ser Ser Pro Val Thr Lys Ser Phe Asn Arg Gly Glu Cys
225                 230                 235
```

<210> SEQ ID NO 4
<211> LENGTH: 238
<212> TYPE: PRT
<213> ORGANISM: Artificial Sequence
<220> FEATURE:
<223> OTHER INFORMATION: Synthetic Construct

<400> SEQUENCE: 4

```
Met Val Leu Gln Thr Gln Val Phe Ile Ser Leu Leu Leu Trp Ile Ser
1               5                   10                  15

Gly Ala Tyr Gly Glu Ile Leu Met Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45
```

```
Val Thr Ile Ser Gly Tyr Ser Phe Ile His Trp Tyr Gln Gln Lys Pro
 50                  55                  60

Gly Gln Ala Pro Arg Leu Leu Ile Tyr Arg Ala Ser Asn Leu Ala Ser
 65                  70                  75                  80

Gly Ile Pro Ala Arg Phe Ser Gly Ser Gly Ser Gly Thr Asp Phe Thr
                 85                  90                  95

Leu Thr Ile Ser Ser Leu Glu Pro Glu Asp Phe Ala Leu Tyr Tyr Cys
            100                 105                 110

Gln Gln Ser Arg Lys Ser Pro Trp Thr Phe Gly Gln Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 5
<211> LENGTH: 1398
<212> TYPE: DNA
<213> ORGANISM: Artificial Sequence
<220> FEATURE:
<223> OTHER INFORMATION: Heavy chain of K3-1115/T103E
<220> FEATURE:
<221> NAME/KEY: CDS
<222> LOCATION: (1)..(1398)

<400> SEQUENCE: 5

```
atg aaa cac ctg tgg ttc ttc ctc ctg ctg gtg gca gct ccc aga tgg       48
Met Lys His Leu Trp Phe Phe Leu Leu Leu Val Ala Ala Pro Arg Trp
1               5                   10                  15 gtg ctg agc gaa gtc cag ctt gtg gaa agc gga ggg gga ctc gtt cag       96
Val Leu Ser Glu Val Gln Leu Val Glu Ser Gly Gly Gly Leu Val Gln
                20                  25                  30 cca gga ggc tct ctg cgc ctg tca tgc gct gcc agc gga ttt aat ttc      144
Pro Gly Gly Ser Leu Arg Leu Ser Cys Ala Ala Ser Gly Phe Asn Phe
            35                  40                  45 aat gat tat ttt atg aac tgg gtc agg cag gct ccg gga aaa ggg ctg      192
Asn Asp Tyr Phe Met Asn Trp Val Arg Gln Ala Pro Gly Lys Gly Leu
 50                  55                  60 gaa tgg gtc gcc cag atc aga aac aag atc tat act tac gct aca ttc      240
Glu Trp Val Ala Gln Ile Arg Asn Lys Ile Tyr Thr Tyr Ala Thr Phe
 65                  70                  75                  80 tac gcc gca tct gta aag ggg agg ttt aca att agt cgc gac aat gca      288
Tyr Ala Ala Ser Val Lys Gly Arg Phe Thr Ile Ser Arg Asp Asn Ala
                 85                  90                  95 aaa aat agt ctg tat ctc caa atg aac tcc ctc cgc gca gag gat act      336
Lys Asn Ser Leu Tyr Leu Gln Met Asn Ser Leu Arg Ala Glu Asp Thr
            100                 105                 110 gct gtc tac tac tgc gcc agg tcc ttg gag ggc ggc gac tat ttt gat      384
Ala Val Tyr Tyr Cys Ala Arg Ser Leu Glu Gly Gly Asp Tyr Phe Asp
```

-continued

```
                  115                 120                 125
tac tgg gga cag ggc acc ctg gtg acg gtg agc tca gcc agc acc aag    432
Tyr Trp Gly Gln Gly Thr Leu Val Thr Val Ser Ser Ala Ser Thr Lys
        130                 135                 140 ggc cct tcc gtg ttc cct ctg gcc cct tgt agc cgt tcc acc agc gag    480
Gly Pro Ser Val Phe Pro Leu Ala Pro Cys Ser Arg Ser Thr Ser Glu
145                 150                 155                 160 tcc acc gcc gcc ctt ggc tgt ctg gtg aag gac tac ttc cct gag cct    528
Ser Thr Ala Ala Leu Gly Cys Leu Val Lys Asp Tyr Phe Pro Glu Pro
                165                 170                 175 gtg acc gtg agc tgg aac tcc gga gcc ctt acc agc ggc gtg cac acc    576
Val Thr Val Ser Trp Asn Ser Gly Ala Leu Thr Ser Gly Val His Thr
            180                 185                 190 ttc cct gcc gtg ctg cag tcc agc ggc ctt tac tcc ctg agc tcc gtg    624
Phe Pro Ala Val Leu Gln Ser Ser Gly Leu Tyr Ser Leu Ser Ser Val
        195                 200                 205 gtg acc gtg cct agc tcc aac ttc ggc acc caa acc tac acc tgt aac    672
Val Thr Val Pro Ser Ser Asn Phe Gly Thr Gln Thr Tyr Thr Cys Asn
    210                 215                 220 gtg gac cac aag cct agc aac acc aag gtg gac aag acc gtg gag cgt    720
Val Asp His Lys Pro Ser Asn Thr Lys Val Asp Lys Thr Val Glu Arg
225                 230                 235                 240 aag tgt tgt gtg gag tgt cct cct tgt cct gcc cct cct gtg gcc gga    768
Lys Cys Cys Val Glu Cys Pro Pro Cys Pro Ala Pro Pro Val Ala Gly
                245                 250                 255 cct tcc gtg ttc ctt ttc cct cct aag cct aag gac acc ctg atg atc    816
Pro Ser Val Phe Leu Phe Pro Pro Lys Pro Lys Asp Thr Leu Met Ile
            260                 265                 270 agc cgt acc cct gag gtg acc tgt gtg gtg gtg gac gtg tcc cac gag    864
Ser Arg Thr Pro Glu Val Thr Cys Val Val Val Asp Val Ser His Glu
        275                 280                 285 gac cct gag gtg cag ttc aac tgg tac gtg gac ggc gtg gag gtg cac    912
Asp Pro Glu Val Gln Phe Asn Trp Tyr Val Asp Gly Val Glu Val His
    290                 295                 300 aac gcc aag acc aag cct cgt gag gag caa ttc aac agc acc ttc cgt    960
Asn Ala Lys Thr Lys Pro Arg Glu Glu Gln Phe Asn Ser Thr Phe Arg
305                 310                 315                 320 gtg gtg tcc gtg ctt acc gtg gtg cac caa gac tgg ctg aac ggc aag   1008
Val Val Ser Val Leu Thr Val Val His Gln Asp Trp Leu Asn Gly Lys
                325                 330                 335 gag tac aag tgt aag gtg agc aac aag gga ctt cct gcc cct atc gag   1056
Glu Tyr Lys Cys Lys Val Ser Asn Lys Gly Leu Pro Ala Pro Ile Glu
            340                 345                 350 aag acc atc tcc aag acc aag ggc caa cct cgt gag cct caa gtg tac   1104
Lys Thr Ile Ser Lys Thr Lys Gly Gln Pro Arg Glu Pro Gln Val Tyr
        355                 360                 365 acc ctt cct cct agc cgt gag gag atg acc aag aac caa gtg tcc ctt   1152
Thr Leu Pro Pro Ser Arg Glu Glu Met Thr Lys Asn Gln Val Ser Leu
    370                 375                 380 acc tgt ctg gtg aag ggc ttc tac cct agc gac atc gcc gtg gag tgg   1200
Thr Cys Leu Val Lys Gly Phe Tyr Pro Ser Asp Ile Ala Val Glu Trp
385                 390                 395                 400 gag tcc aac gga caa cct gag aac aac tac aag acc acc cct cct atg   1248
Glu Ser Asn Gly Gln Pro Glu Asn Asn Tyr Lys Thr Thr Pro Pro Met
                405                 410                 415 ctt gac agc gac ggc tcc ttc ttc ctg tac agc aag ctg acc gtg gac   1296
Leu Asp Ser Asp Gly Ser Phe Phe Leu Tyr Ser Lys Leu Thr Val Asp
            420                 425                 430 aag tcc cgt tgg caa caa ggc aac gtg ttc agc tgt tcc gtg atg cac   1344
```

```
Lys Ser Arg Trp Gln Gln Gly Asn Val Phe Ser Cys Ser Val Met His
            435                 440                 445 gag gcc ctg cac aac cac tac acc caa aag agc ctt tcc ctg agc cct      1392
Glu Ala Leu His Asn His Tyr Thr Gln Lys Ser Leu Ser Leu Ser Pro
    450                 455                 460 gga aag                                                              1398
Gly Lys
465

<210> SEQ ID NO 6
<211> LENGTH: 466
<212> TYPE: PRT
<213> ORGANISM: Artificial Sequence
<220> FEATURE:
<223> OTHER INFORMATION: Synthetic Construct

<400> SEQUENCE: 6

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys Ile Tyr Thr Tyr Ala Thr Phe
65                  70                  75                  80

Tyr Ala Ala Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Ser Leu Glu Gly Gly Asp Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
```

```
                 305                 310                 315                 320

Val Val Ser Val Leu Thr Val Val His Gln Asp Trp Leu Asn Gly Lys
                        325                 330                 335

Glu Tyr Lys Cys Lys Val Ser Asn Lys Gly Leu Pro Ala Pro Ile Glu
                        340                 345                 350

Lys Thr Ile Ser Lys Thr Lys Gly Gln Pro Arg Glu Pro Gln Val Tyr
                        355                 360                 365

Thr Leu Pro Pro Ser Arg Glu Glu Met Thr Lys Asn Gln Val Ser Leu
                        370                 375                 380

Thr Cys Leu Val Lys Gly Phe Tyr Pro Ser Asp Ile Ala Val Glu Trp
        385                 390                 395                 400

Glu Ser Asn Gly Gln Pro Glu Asn Asn Tyr Lys Thr Pro Pro Met
                        405                 410                 415

Leu Asp Ser Asp Gly Ser Phe Phe Leu Tyr Ser Lys Leu Thr Val Asp
                        420                 425                 430

Lys Ser Arg Trp Gln Gln Gly Asn Val Phe Ser Cys Ser Val Met His
                        435                 440                 445

Glu Ala Leu His Asn His Tyr Thr Gln Lys Ser Leu Ser Leu Ser Pro
                        450                 455                 460

Gly Lys
        465

<210> SEQ ID NO 7
<211> LENGTH: 5
<212> TYPE: PRT
<213> ORGANISM: Rattus norvegicus

<400> SEQUENCE: 7

Asp Tyr Phe Met Asn
1               5

<210> SEQ ID NO 8
<211> LENGTH: 19
<212> TYPE: PRT
<213> ORGANISM: Rattus norvegicus

<400> SEQUENCE: 8

Gln Ile Arg Asn Lys Ile Tyr Thr Tyr Ala Thr Phe Tyr Ala Glu Ser
1               5                   10                  15

Leu Glu Gly

<210> SEQ ID NO 9
<211> LENGTH: 14
<212> TYPE: PRT
<213> ORGANISM: Rattus norvegicus

<400> SEQUENCE: 9

Gln Ile Arg Asn Lys Ile Tyr Thr Tyr Ala Thr Phe Tyr Ala
1               5                   10

<210> SEQ ID NO 10
<211> LENGTH: 10
<212> TYPE: PRT
<213> ORGANISM: Rattus norvegicus

<400> SEQUENCE: 10

Ser Leu Thr Gly Gly Asp Tyr Phe Asp Tyr
1               5                   10
```

```
<210> SEQ ID NO 11
<211> LENGTH: 10
<212> TYPE: PRT
<213> ORGANISM: Artificial Sequence
<220> FEATURE:
<223> OTHER INFORMATION: CDRH3 of K3-1115/T103E

<400> SEQUENCE: 11

Ser Leu Glu Gly Gly Asp Tyr Phe Asp Tyr
1               5                   10

<210> SEQ ID NO 12
<211> LENGTH: 15
<212> TYPE: PRT
<213> ORGANISM: Rattus norvegicus

<400> SEQUENCE: 12

Arg Ala Ser Gln Ser Val Thr Ile Ser Gly Tyr Ser Phe Ile His
1               5                   10                  15

<210> SEQ ID NO 13
<211> LENGTH: 7
<212> TYPE: PRT
<213> ORGANISM: Rattus norvegicus

<400> SEQUENCE: 13

Arg Ala Ser Asn Leu Ala Ser
1               5

<210> SEQ ID NO 14
<211> LENGTH: 9
<212> TYPE: PRT
<213> ORGANISM: Rattus norvegicus

<400> SEQUENCE: 14

Gln Gln Ser Arg Lys Ser Pro Trp Thr
1               5

<210> SEQ ID NO 15
<211> LENGTH: 34
<212> TYPE: DNA
<213> ORGANISM: Artificial Sequence
<220> FEATURE:
<223> OTHER INFORMATION: PCR primer 32A1_HT103EFw

<400> SEQUENCE: 15
ctactactgc gccaggtcct tggagggcgg cgac                              34

<210> SEQ ID NO 16
<211> LENGTH: 34
<212> TYPE: DNA
<213> ORGANISM: Artificial Sequence
<220> FEATURE:
<223> OTHER INFORMATION: PCR primer 32A1_HT103ERv

<400> SEQUENCE: 16
gtcgccgccc tccaaggacc tggcgcagta gtag                              34
```